US011026560B2

(12) United States Patent
Yamada

(10) Patent No.: US 11,026,560 B2
(45) Date of Patent: Jun. 8, 2021

(54) MEDICAL DISPLAY CONTROL APPARATUS AND DISPLAY CONTROL METHOD

(71) Applicant: Sony Olympus Medical Solutions Inc., Tokyo (JP)

(72) Inventor: Takaaki Yamada, Kanagawa (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 92 days.

(21) Appl. No.: 16/274,300

(22) Filed: Feb. 13, 2019

(65) Prior Publication Data

US 2019/0282067 A1   Sep. 19, 2019

(30) Foreign Application Priority Data

Mar. 15, 2018   (JP) .............................. JP2018-047627

(51) Int. Cl.
*A61B 1/00* (2006.01)
*G02B 21/00* (2006.01)
(Continued)

(52) U.S. Cl.
CPC ...... *A61B 1/00045* (2013.01); *A61B 1/00193* (2013.01); *A61B 1/04* (2013.01);
(Continued)

(58) Field of Classification Search
CPC ............ A61B 1/00009; A61B 1/00045; A61B 1/0005; A61B 1/00188; A61B 1/00193; A61B 1/04; A61B 1/0638; A61B 1/0646; A61B 1/0661; A61B 2017/00203; A61B 2017/00207; A61B 2017/00212; A61B 2017/00429; A61B 2017/00734; A61B 2017/00793; A61B 2034/2059; A61B 2090/304; A61B 2090/371; A61B 2090/372; A61B 2090/502; A61B 2090/508; A61B 34/25; A61B 90/25; A61B 90/30; A61B 90/361; A61B 90/37; A61B 90/50; A61B 90/92; A61B 2034/101; A61B 8/4245; G02B 2027/0185; G02B 21/0012; G02B 21/22; G02B 21/365; G09G 5/377
(Continued)

(56) References Cited

U.S. PATENT DOCUMENTS

2009/0036902 A1* 2/2009 DiMaio .................. A61B 34/37
606/130
2012/0050277 A1* 3/2012 Murakoshi ........... H04N 13/398
345/419
(Continued)

FOREIGN PATENT DOCUMENTS

JP    2004-223128       8/2004
WO   WO-2016158000 A1 * 10/2016 ............... G09G 5/00

*Primary Examiner* — Nathnael Aynalem
(74) *Attorney, Agent, or Firm* — Xsensus LLP

(57) ABSTRACT

There is provided a medical display control apparatus including: a display control section configured to control a display of a medical captured image for a right eye and a medical captured image for a left eye captured by an imaging device that images an observation target on a display screen and a display of a pointer object on the display screen. The display control section causes the pointer object to be displayed in correspondence with a depth position of the medical captured image for the right eye and the medical captured image for the left eye.

16 Claims, 7 Drawing Sheets

(51) Int. Cl.
  *A61B 1/04* (2006.01)
  *A61B 90/30* (2016.01)
  *A61B 1/06* (2006.01)
  *A61B 90/50* (2016.01)
  *A61B 90/00* (2016.01)
  *A61B 90/92* (2016.01)

(52) U.S. Cl.
  CPC .......... *A61B 90/30* (2016.02); *G02B 21/0012* (2013.01); *A61B 1/00009* (2013.01); *A61B 1/0638* (2013.01); *A61B 1/0646* (2013.01); *A61B 1/0661* (2013.01); *A61B 90/361* (2016.02); *A61B 90/37* (2016.02); *A61B 90/50* (2016.02); *A61B 90/92* (2016.02); *A61B 2090/502* (2016.02)

(58) Field of Classification Search
  USPC .......................................................... 348/65
  See application file for complete search history.

(56) References Cited

U.S. PATENT DOCUMENTS

| | | | |
|---|---|---|---|
| 2012/0069159 A1* | 3/2012 | Matsui | H04N 13/398 348/51 |
| 2017/0280989 A1* | 10/2017 | Heeren | G02B 21/0012 |
| 2018/0276898 A1* | 9/2018 | Nishizawa | G06T 19/006 |
| 2019/0015163 A1* | 1/2019 | Abhari | A61B 34/20 |

\* cited by examiner

FIG. 6
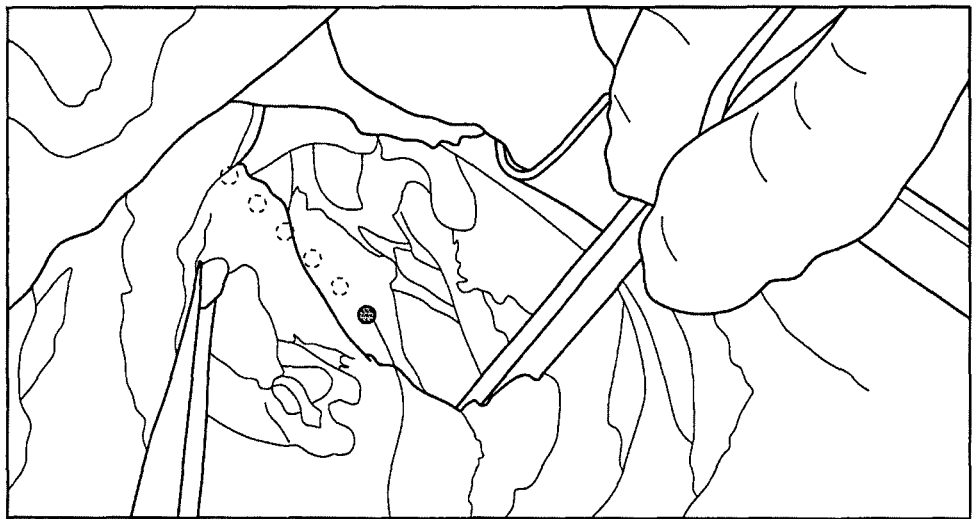
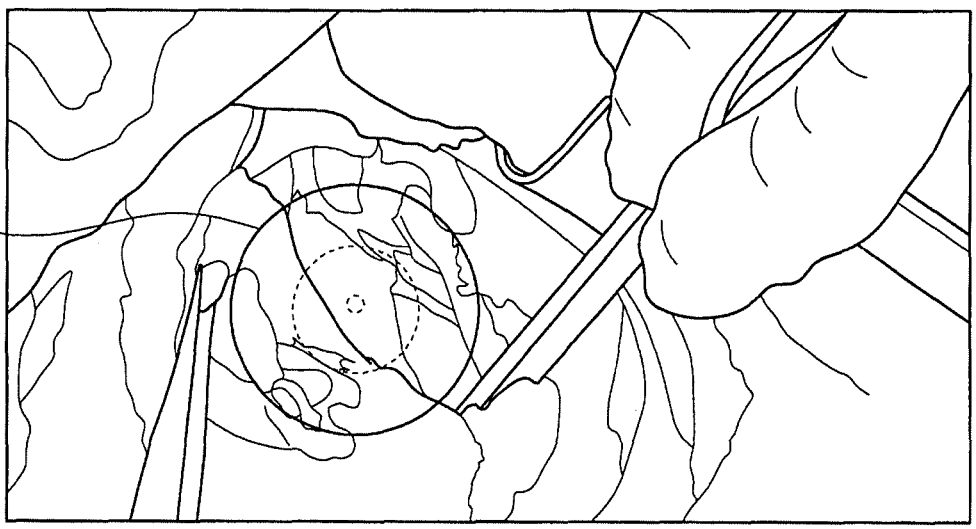
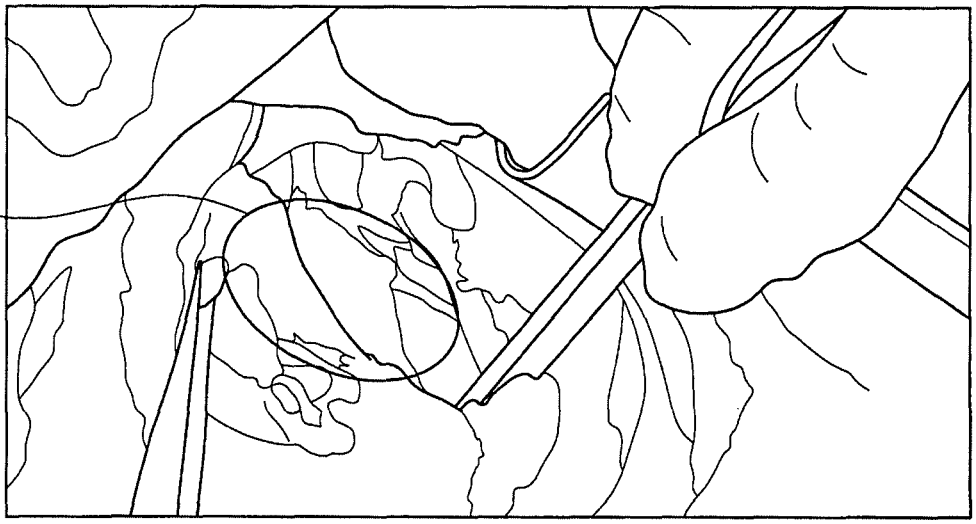

MEDICAL DISPLAY CONTROL APPARATUS AND DISPLAY CONTROL METHOD

CROSS REFERENCE TO RELATED APPLICATIONS

This application claims the benefit of Japanese Priority Patent Application JP 2018-047627 filed Mar. 15, 2018, the entire contents of which are incorporated herein by reference.

BACKGROUND

The present disclosure relates to a medical display control apparatus and a display control method.

Recently, in the medical field, to support microsurgery such as neurosurgical procedures, or to perform an endoscopic surgery, for example, medical observation apparatus capable of enlarged observation of an observation target such as an affected area are used in some cases. Examples of medical observation apparatus include a medical observation apparatus provided with an optical microscope, and a medical observation apparatus provided with an imaging device that functions as an electronic imaging microscope. In the following, the above medical observation apparatus provided with an optical microscope will be designated an "optical medical observation apparatus". Also, in the following, the above medical observation apparatus provided with an imaging device will be designated an "electronic imaging medical observation apparatus" or simply a "medical observation apparatus" in some cases. Also, in the following, a captured image (a moving image or a still image; the same applies hereinafter) in which an observation target is captured by an imaging device provided in a medical observation apparatus is denoted a "medical captured image".

With an electronic imaging medical observation apparatus, along with the increased image quality of imaging devices, the increased image quality of display apparatus on which captured images are displayed, and the like, the same or higher image quality than an optical medical observation apparatus has come to be obtained. Also, because a user who uses an electronic imaging medical observation apparatus (for example, medical personnel such as a surgeon or a surgeon's assistant; the same applies hereinafter) is not required to peer into an eyepiece lens included in an optical microscope like in the case of using an optical medical observation apparatus, it is possible to move the position of the imaging device more freely. For this reason, using an electronic imaging medical observation apparatus has an advantage of enabling more flexible support of microsurgery, and in the medical field, utilization of electronic imaging medical observation apparatus is progressing.

Among these, technology enabling confirmation of whether or not a position with respect to a medical treatment site of a medical instrument is inside a predetermined range or on a predetermined path is being developed. An example of the above technology includes the technology described in JP 2004-223128A.

SUMMARY

In the case in which an electronic imaging medical observation apparatus is used in the medical field, a medical captured image displayed on a display screen of a display apparatus is viewed at the same time by multiple persons, such as the surgeon, an assistant, a nurse, and an attending physician. Also, in the above case, when one person attempts to inform another person of a specific location to pay attention to in the medical captured image being displayed on the display screen, oral instructions are used. However, with verbal communication such as oral instructions, it may be difficult to convey the above location of attention appropriately in some cases.

The present disclosure proposes a novel and improved medical display control apparatus and display control method capable of potentially improving convenience for persons viewing a display screen on which a medical captured image is displayed.

According to an embodiment of the present disclosure, there is provided a medical display control apparatus including: a display control section configured to control a display of a medical captured image for a right eye and a medical captured image for a left eye captured by an imaging device that images an observation target on a display screen and a display of a pointer object on the display screen. The display control section causes the pointer object to be displayed in correspondence with a depth position of the medical captured image for the right eye and the medical captured image for the left eye.

In addition, according to an embodiment of the present disclosure, there is provided a display control method executed by a medical display control apparatus, the display control method including: controlling a display of a medical captured image for a right eye and a medical captured image for a left eye captured by an imaging device that images an observation target on a display screen and a display of a pointer object on the display screen. The controlling causes the pointer object to be displayed in correspondence with a depth position of the medical captured image for the right eye and the medical captured image for the left eye.

According to an embodiment of the present disclosure, improved convenience for persons viewing a display screen on which a medical captured image is displayed may be achieved.

Note that the effects described above are not necessarily limitative. With or in the place of the above effects, there may be achieved any one of the effects described in this specification or other effects that may be grasped from this specification.

BRIEF DESCRIPTION OF THE DRAWINGS

FIG. 6 is an explanatory diagram for explaining a first example of processes related to the display control method according to the present embodiment.

DETAILED DESCRIPTION OF THE EMBODIMENT(S)

Figure 1:
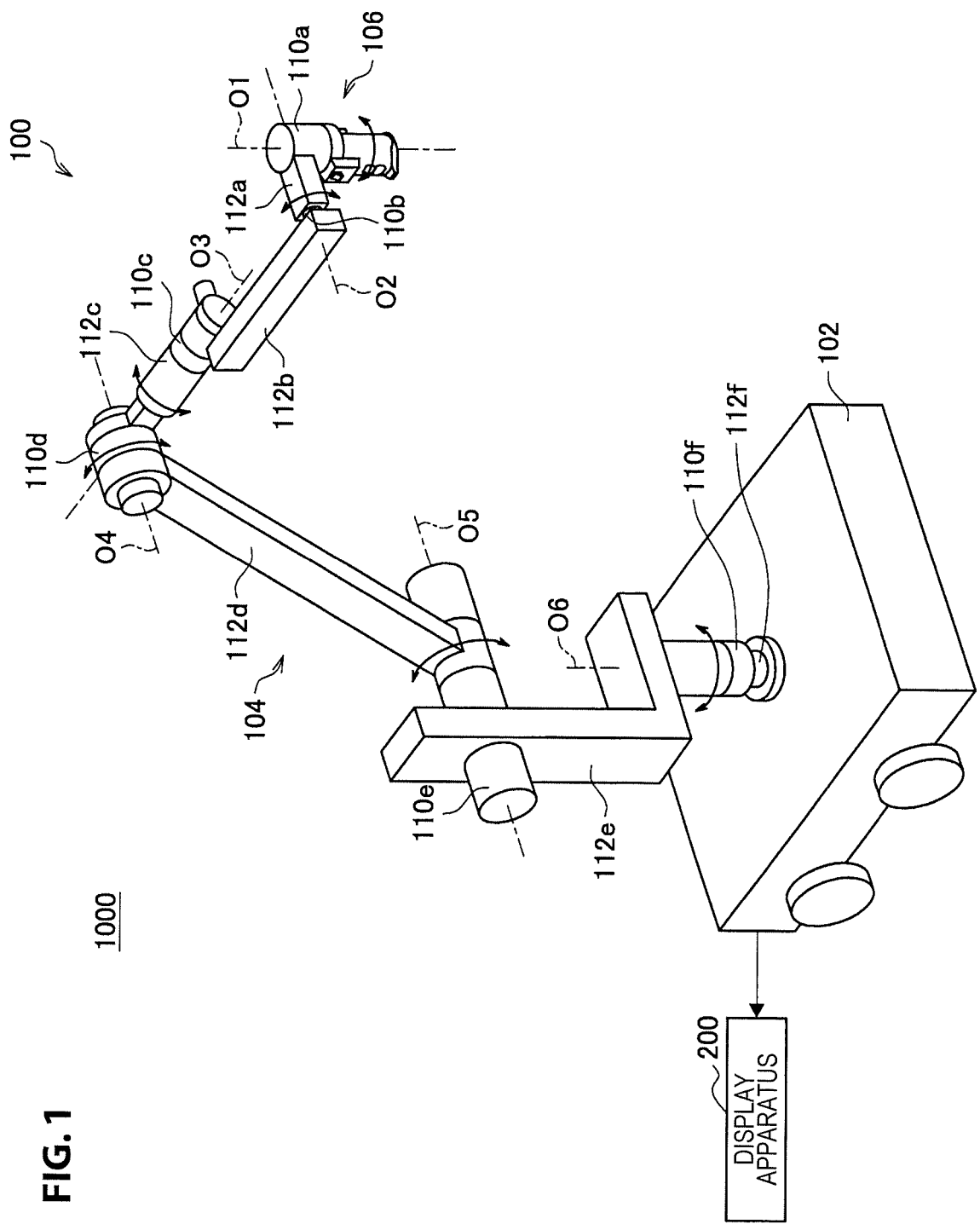
FIG. 1 is an explanatory diagram illustrating a first example of a configuration of a medical observation system according to the present embodiment.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

The description hereinafter will proceed in the following order.

1. Medical observation system according to present embodiment and display control method according to present embodiment
    [1] Configuration of medical observation system
        [1-1] Medical observation system according to first example
        [1-2] Medical observation system according to second example
        [1-3] Functional configuration of medical observation apparatus
    [2] Display control method according to present embodiment
        [2-1] Processes related to display control method according to present embodiment
        [2-2] Example of processes related to display control method according to present embodiment
    [3] Example of advantageous effects exhibited by use of display control method according to present embodiment
2. Program according to present embodiment (Medical Observation System According to Present Embodiment and Display Control Method According to Present Embodiment)

Hereinafter, an example of a medical observation system according to the present embodiment will be described, while a display control method according to the present embodiment will also be described.

Hereinafter, the case in which the medical observation apparatus according to the present embodiment executes processes related to the display control method according to the present embodiment, that is, the case in which the medical observation apparatus according to the present embodiment functions as a medical display control apparatus will be described primarily. Note that in the medical observation system according to the present embodiment, the apparatus that functions as the medical display control apparatus is not limited to the medical observation apparatus according to the present embodiment. For example, in the medical observation system according to the present embodiment, the display apparatus described later may also function as the medical display control apparatus that executes the processes related to the display control method according to the present embodiment. For example, in the medical observation system according to the present embodiment, any apparatus capable of executing the processes related to the display control method according to the present embodiment, such as a medical controller, may function as the medical display control apparatus.

[1] Configuration of medical observation system
[1-1] Medical observation system according to first example FIG. 1 is an explanatory diagram illustrating a first example of the configuration of a medical observation system 1000 according to the present embodiment. The medical observation system 1000 illustrated in FIG. 1 includes a medical observation apparatus 100 and a display apparatus 200, for example.

Note that the medical observation system according to the first example is not limited to the example illustrated in FIG. 1.

For example, the medical observation system according to the first example additionally may include a medical control apparatus (not illustrated) that controls various operations in the medical observation apparatus 100. In the medical observation system 1000 illustrated in FIG. 1, as described later, an example is illustrated in which, by providing the medical observation apparatus 100 with a control section (described later), the medical observation apparatus 100 includes the functions of the medical control apparatus (not illustrated).

Examples of the medical control apparatus (not illustrated) include, a "medical controller", a "computer such as a server", and the like. Also, the medical control apparatus (not illustrated) may be, for example, an integrated circuit (IC) that can be embedded in equipment like the above.

Additionally, the medical observation system according to the first example may also be a configuration that includes one or both of the medical observation apparatus 100 and the display apparatus 200. In the case of including multiple medical observation apparatuses 100, in each medical observation apparatus 100, processes according to the display control method described later are performed. Also, in the case in which the medical observation system according to the first example is a configuration that includes multiple medical observation apparatuses 100 and display apparatuses 200, the medical observation apparatus 100 and the display apparatus 200 may be associated in a 1-to-1 manner, or multiple medical observation apparatuses 100 may be associated with a single display apparatus 200. In the case in which multiple medical observation apparatuses 100 are associated with a single display apparatus 200, which medical observation apparatus 100 provides a medical captured image to be displayed on a display screen is switched by performing a switching operation or the like in the display apparatus 200, for example.

Figure 2:
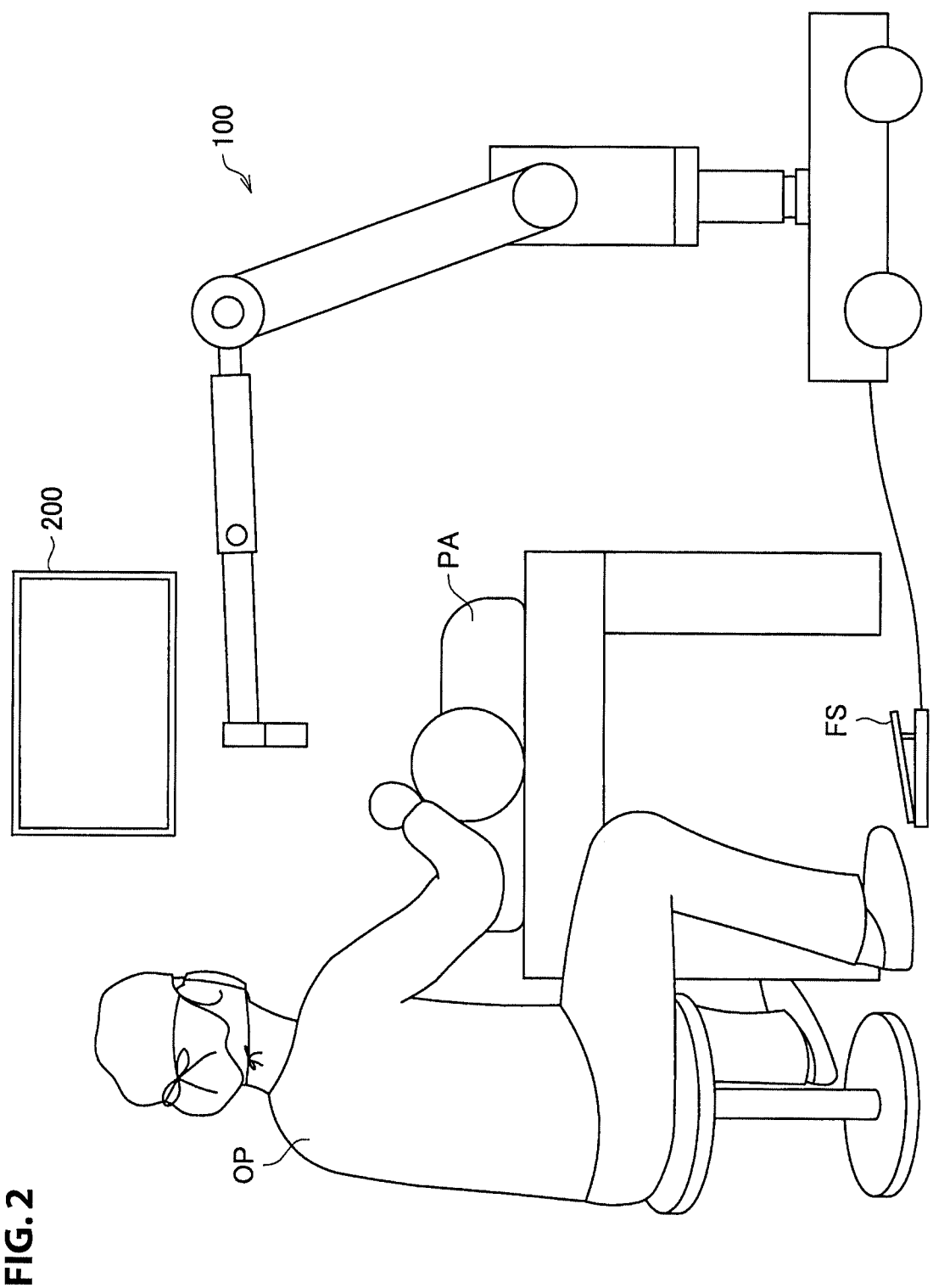
FIG. 2 is an explanatory diagram illustrating an example of a use case in which the medical observation system according to the present embodiment is used.

FIG. 2 is an explanatory diagram illustrating one example of a use case in which the medical observation system 1000 according to the present embodiment is used, and illustrates one example of a use case in which the medical observation system 1000 according to the first example is used.

By an imaging device (described later) provided in the medical observation apparatus 100, an observation target patient PA (a patient who undergoes a medical procedure) is imaged. A captured image that captures the above patient who undergoes a medical procedure, corresponds to an example of a "medical captured image".

The medical captured image captured in the medical observation apparatus 100 is displayed on a display screen of a display apparatus 200. Subsequently, a surgeon OP (an example of a user of the medical observation apparatus 100) who performs a medical procedure by using the medical observation apparatus 100 performs the medical procedure on the patient PA while looking at the medical captured image displayed on the display screen of the display apparatus 200.

Also, the surgeon OP operates an operating device external to the medical observation apparatus 100, such as a footswitch FS, or an operating device (described later) provided in the medical observation apparatus 100, thereby causing an arm (described later) and the imaging device (described later) provided in the medical observation apparatus 100 to operate, and putting the medical observation apparatus 100 into a desired state.

Hereinafter, each apparatus included in the medical observation system 1000 according to the first example illustrated in FIG. 1 will be described.

[1-1-1] Display Apparatus 200

The display apparatus 200 is a display device in the medical observation system 1000 according to the first example, and corresponds to an external display device from the perspective of the medical observation apparatus 100. The display apparatus 200 displays various images on a display screen, such as a medical captured image taken in the medical observation apparatus 100, or an image related to a user interface (UI), for example. Also, the display apparatus 200 may include a configuration capable of 3D display according to any method. The display on the display apparatus 200 is controlled by, for example, the medical observation apparatus 100 or the medical control apparatus (not illustrated).

In the medical observation system 1000, the display apparatus 200 is installed in an arbitrary location visible to a person involved in a surgery inside an operating room, such as on a wall, the ceiling, or the floor of the operating room.

Examples of the display apparatus 200 include a liquid crystal display, an organic electro-luminescence (EL) display, a cathode ray tube (CRT) display, and the like.

Note that the display apparatus 200 is not limited to the example illustrated above. For example, the display apparatus 200 may also be an arbitrary wearable apparatus that is used by being worn on the body of the surgeon or the like, such as a head-mounted display, an eyewear-type apparatus, or the like.

The display apparatus 200 runs on electric power supplied from an internal power source such as a battery provided in the display apparatus 200, on electric power supplied from a connected external power source, or the like, for example.

[1-1-2] Medical Observation Apparatus 100

The medical observation apparatus 100 illustrated in FIG. 1 is an electronic imaging medical observation apparatus. For example, in the case in which the medical observation apparatus 100 illustrated in FIG. 1 is used during surgery, the surgeon (one example of the user of the medical observation apparatus 100) observes an operating site (an affected area) while referring to a medical captured image which has been taken by the medical observation apparatus 100 and displayed on the display screen of the display apparatus 200, and performs various treatments, such as techniques depending on the surgical procedure, on the operating site.

As illustrated in FIG. 1, the medical observation apparatus 100 is provided with a base 102, an arm 104, and an imaging device 106, for example.

Additionally, although not illustrated in FIG. 1, the medical observation apparatus 100 may also be provided with, for example, one or multiple processors (not illustrated) including a computational circuit such as a microprocessing unit (MPU), read-only memory (ROM; not illustrated), random access memory (RAM; not illustrated), a recording medium (not illustrated), and a communication device (not illustrated). The medical observation apparatus 100 runs on electric power supplied from an internal power source such as a battery provided in the medical observation apparatus 100, on electric power supplied from a connected external power source, or the like, for example.

The one or multiple processors (not illustrated) function as the control section in the medical observation apparatus 100 (described later). The ROM (not illustrated) stores programs and control data such as computational parameters used by the one or multiple processors (not illustrated). The RAM (not illustrated) temporarily stores programs executed by the one or multiple processors (not illustrated), or the like.

The recording medium (not illustrated) functions as a storage section (not illustrated) in the medical observation apparatus 100. A variety of data is stored on the recording medium (not illustrated), including data related to the display control method according to the present embodiment, and various applications, for example. Herein, examples of the recording medium (not illustrated) include a magnetic recording medium such as a hard disk, non-volatile memory such as flash memory, and the like. Additionally, the recording medium (not illustrated) may also be removable from the medical observation apparatus 100.

The communication device (not illustrated) is a communication device provided in the medical observation apparatus 100, and fulfills a role of communicating in a wireless or wired manner with an external apparatus such as the display apparatus 200. Herein, examples of the communication device (not illustrated) include an IEEE 802.15.1 port and transmitting-receiving circuit (wireless communication), an IEEE 802.11 port and transmitting-receiving circuit (wireless communication), a communication antenna and a RF circuit (wireless communication), a LAN terminal and a transmitting-receiving circuit (wired communication), and the like.

[1-1-2-1] Base 102

The base 102 is the base of the medical observation apparatus 100. One end of the arm 104 is connected to the base 102, and the base 102 supports the arm 104 and the imaging device 106.

Also, casters are provided on the base 102, for example, and the medical observation apparatus 100 contacts the floor through the casters. By providing the casters, the medical observation apparatus 100 is able to move easily over the floor by the casters.

[1-1-2-2] Arm 104

The arm 104 includes multiple links joined to each other by joint sections.

In addition, the arm 104 supports the imaging device 106. The imaging device 106 supported by the arm 104 is movable three-dimensionally, and after moving, the position and the attitude of the imaging device 106 are maintained by the arm 104.

More specifically, the arm 104 includes, for example, multiple joint sections 110a, 110b, 110c, 110d, 110e, and 110f, and multiple links 112a, 112b, 112c, 112d, 112e, and 112f rotatably joined to each other by the joint sections 110a, 110b, 110c, 110d, 110e, and 110f. The rotatable range of each of the joint sections 110a, 110b, 110c, 110d, 110e, and 110f is set arbitrarily during the design stage, the manufacturing stage, or the like so that the desired motion of the arm 104 is realized.

In other words, in the medical observation apparatus 100 illustrated in FIG. 1, six degrees of freedom are realized in relation to the movement of the imaging device 106 by six rotation axes (first axis O1, second axis O2, third axis O3, fourth axis O4, fifth axis O5, and sixth axis O6) corresponding to the six joint sections 110a, 110b, 110c, 110d, 110e, and 110*f* included in the arm 104. More specifically, in the medical observation apparatus 100 illustrated in FIG. 1, motion with six degrees of freedom, including three degrees of translational freedom and three degrees of rotational freedom, is realized.

Actuators (not illustrated) are provided in each of the joint sections 110*a*, 110*b*, 110*c*, 110*d*, 110*e*, and 110*f*. Each of the joint sections 110*a*, 110*b*, 110*c*, 110*d*, 110*e*, and 110*f* rotates about the corresponding rotation axis by the driving of the actuators (not illustrated). The driving of the actuators (not illustrated) is controlled by, for example, a processor that functions as the control section described later, or an external medical control apparatus (not illustrated).

Each of the joint sections 110*a*, 110*b*, 110*c*, 110*d*, 110*e*, and 110*f* may be provided with angle sensors (not illustrated) capable of detecting a rotational angle for each of six rotation axes. The angle sensors may be, for example, rotary encoders, or any sensors capable of obtaining a rotational angle for each of six rotation axes, such as angular velocity sensors.

By having each of the joint sections 110*a*, 110*b*, 110*c*, 110*d*, 110*e*, 110*f* rotate about the corresponding rotation axis by the driving of the actuators (not illustrated), various operations of the arm 104, such as extending and contracting (folding up) the arm 104, for example, are realized.

The joint section 110*a* has an approximately cylindrical shape, and supports the imaging device 106 (the top end of the imaging device 106 in FIG. 1) on the front end portion of the joint section 110*a* (the bottom end portion in FIG. 1), so as to allow revolution about a rotation axis (first axis O1) parallel to the central axis of the imaging device 106. Herein, the medical observation apparatus 100 is configured so that the first axis O1 is aligned with the optical axis in the imaging device 106. In other words, by causing the imaging device 106 to revolve about the first axis O1 illustrated in FIG. 1, the medical captured image captured by the imaging device 106 becomes an image which has changed so that the field of view rotates.

The link 112*a* is an approximately rod-shaped member, and securely supports the joint section 110*a*. The link 112*a* extends in a direction orthogonal to the first axis O1, for example, and is connected to the joint section 110*b*.

The joint section 110*b* has an approximately cylindrical shape, and supports the link 112*a* so as to allow revolution about a rotation axis (second axis O2) orthogonal to the first axis O1. Also, the link 112*b* is securely connected to the joint section 110*b*.

The link 112*b* is an approximately rod-shaped member, and extends in a direction orthogonal to the second axis O2. Also, each of the joint section 110*b* and the joint section 110*c* is connected to the link 112*b*.

The joint section 110*c* has an approximately cylindrical shape, and supports the link 112*b* so as to allow revolution about a rotation axis (third axis O3) mutually orthogonal to each of the first axis O1 and the second axis O2. Also, one end of the link 112*c* is securely connected to the joint section 110*c*.

Herein, by having the front end side (the side on which the imaging device 106 is provided) of the arm 104 revolve about the second axis O2 and the third axis O3, the imaging device 106 can be made to move so that the position of the imaging device 106 in the horizontal plane is changed. In other words, in the medical observation apparatus 100, controlling the rotation about the second axis O2 and the third axis O3 makes it possible to move the field of view of the medical captured image in a flat plane.

The link 112*c* is a member in which one end has an approximately cylindrical shape, and the other end has an approximately rod-like shape. On the side of the one end of the link 112*c*, the joint section 110*c* is securely connected so that the central axis of the joint section 110*c* and the central axis of the approximately cylindrical shape are the same. Also, on the side of the other end of the link 112*c*, the joint section 110*d* is connected.

The joint section 110*d* has an approximately cylindrical shape, and supports the link 112*c* so as to allow revolution about a rotation axis (fourth axis O4) orthogonal to the third axis O3. The link 112*d* is securely connected to the joint section 110*d*.

The link 112*d* is an approximately rod-shaped member, and extends orthogonally to the fourth axis O4. One end of the link 112*d* is securely connected to the joint section 110*d* so as to abut the approximately cylindrical side face of the joint section 110*d*. Also, the joint section 110*e* is connected to the other end of the link 112*d* (the end on the opposite side of the side where the joint section 110*d* is connected).

The joint section 110*e* has an approximately cylindrical shape, and supports one end of the link 112*d* so as to allow revolution about a rotation axis (fifth axis O5) parallel to the fourth axis O4. Also, one end of the link 112*e* is securely connected to the joint section 110*e*.

Herein, the fourth axis O4 and the fifth axis O5 are rotation axis about which the imaging device 106 may be moved in the vertical direction. By having the front end side (the side on which the imaging device 106 is provided) of the arm 104 revolve about the fourth axis O4 and the fifth axis O5, the position of the imaging device 106 in the vertical direction changes. Thus, by having the front end side (the side on which the imaging device 106 is provided) of the arm 104 revolve about the fourth axis O4 and the fifth axis O5, changing the distance between the imaging device 106 and an observation target, such as an operating site of a patient, becomes possible.

The link 112*e* is a member that includes a combination of a first member having an approximate L-shape with one edge extending in the vertical direction while the other edge extends in the horizontal direction, and a rod-like second member that extends vertically downward from the part of the first member that extends in the horizontal direction. The joint section 110*e* is securely connected to the part of the first member of the link 112*e* that extends in the vertical direction. Also, the joint section 110*f* is connected to the second member of the link 112*e*.

The joint section 110*f* has an approximately cylindrical shape, and supports the link 112*e* so as to allow revolution about a rotation axis (sixth axis O6) parallel to the vertical direction. Also, the link 112*f* is securely connected to the joint section 110*f*.

The link 112*f* is an approximately rod-shaped member, and extends in the vertical direction. The joint section 110*f* is connected to one end of the link 112*f*. Also, the other end of the link 112*f* (the end on the opposite side of the side where the joint section 110*f* is connected) is securely connected to the base 102.

By having the arm 104 include the configuration indicated above, in the medical observation apparatus 100, six degrees of freedom are realized with respect to the movement of the imaging device 106.

Note that the configuration of the arm 104 is not limited to the example indicated above.

For example, each of the joint sections 110*a*, 110*b*, 110*c*, 110*d*, 110*e*, and 110*f* of the arm 104 may be provided with a brake that restrains rotation in each of the joint sections

110*a*, 110*b*, 110*c*, 110*d*, 110*e*, and 110*f*. The brake according to the present embodiment may be a brake of an arbitrary method, such as a mechanically driven brake or an electrically driven electromagnetic brake, for example.

The driving of the above brakes is controlled by, for example, a processor that functions as the control section described later, or an external medical control apparatus (not illustrated). By controlling the driving of the above brakes, in the medical observation apparatus 100, the operating mode of the arm 104 is set. Examples of operating modes of the arm 104 include a locked mode and a free mode.

Herein, the locked mode according to the present embodiment is, for example, an operating mode in which the position and the attitude of the imaging device 106 are locked by using brakes to restrain rotation about each rotation axis provided in the arm 104. By having the arm 104 enter the locked mode, the operating state of the medical observation apparatus 100 becomes a locked state in which the position and the attitude of the imaging device 106 are locked.

Also, the free mode according to the present embodiment is an operating mode in which the above brakes are released, thereby allowing each rotation axis provided in the arm 104 to rotate freely. For example, in the free mode, the position and the attitude of the imaging device 106 are adjustable by direct operations performed by the surgeon. Herein, a direct operation according to the present embodiment means, for example, an operation in which the surgeon grips the imaging device 106 with his or her hand, and directly moves the imaging device 106.

[1-1-2-3] Imaging Device 106

The imaging device 106 is supported by the arm 104, and images an observation target such as an operating site of a patient, for example. Imaging in the imaging device 106 is controlled by, for example, a processor that functions as the control section described later, or an external medical control apparatus (not illustrated).

The imaging device 106 has a configuration corresponding to an electronic imaging microscope, for example.

Figure 3:
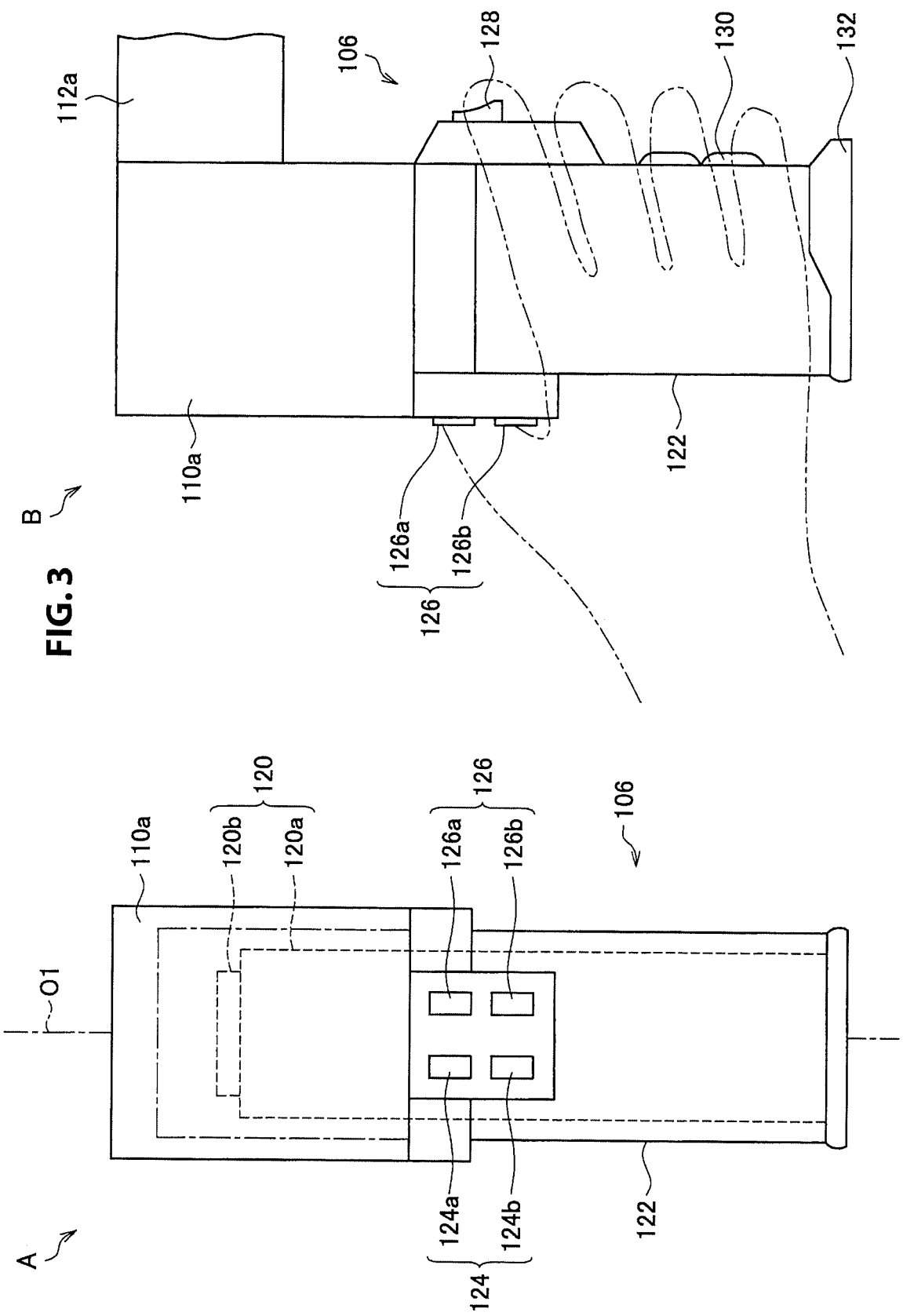
FIG. 3 is an explanatory diagram for explaining an example of the configuration of an imaging device provided in a medical observation apparatus according to the present embodiment.

FIG. 3 is an explanatory diagram for explaining an example of the configuration of the imaging device 106 provided in the medical observation apparatus 100 according to the present embodiment.

For example, the imaging device 106 includes an imaging member 120 and a barrel member 122 having an approximately cylindrical shape, with the imaging member 120 being provided inside the barrel member 122.

On an aperture on the bottom end of the barrel member 122 (the lower end in FIG. 3), for example, a cover glass (not illustrated) for protecting the imaging member 120 is provided.

Additionally, for example, a light source (not illustrated) is provided inside the barrel member 122, and during imaging, the subject is irradiated with illuminating light radiating from the light source through the cover glass. Reflected light (observation light) from the subject irradiated with illuminating light enters the imaging member 120 through the cover glass (not illustrated), whereby an image signal indicating the subject (an image signal indicating a medical captured image) is obtained by the imaging member 120.

As the imaging member 120, any of various known types of configurations used in an electronic imaging microscope section can be applied.

To give one example, the imaging member 120 includes an optical system 120*a* and an image sensor 120*b* including an imaging element that takes an image of an observation target with light transmitted through the optical system 120*a*, for example. The optical system 120*a* includes optical elements such as a mirror and one or multiple lenses, such as an objective lens, a zoom lens, and a focus lens, for example. Examples of the image sensor 120*b* include an image sensor using multiple imaging elements, such as a complementary metal-oxide semiconductor (CMOS) or a charge-coupled device (CCD).

The imaging member 120, by including two or more imaging devices provided with an optical system 120*a* and an image sensor 120*b*, for example, functions as what is called a stereo camera. In the configuration of the imaging device 106 that functions as a stereo camera, the optical system may be a Galileo optical system or a Greenough optical system.

The following gives an example of a case in which the medical observation apparatus 100 according to the present embodiment, including the medical observation apparatus 100 included in the medical observation system according to the second example described later, is provided with multiple imaging devices that function as a stereo camera, and multiple medical captured images, including a medical captured image for the right eye and a medical captured image for the left eye, are obtained.

Each imaging device included in the imaging member 120 is equipped with one or multiple functions typically provided in an electronic imaging microscope section, such as a zoom function (one or both of an optical zoom function and an electronic zoom function) and an autofocus (AF) function.

In addition, the imaging member 120 may also be configured to be capable of imaging at what are called high resolutions, such as 4K and 8K, for example. By configuring the imaging member 120 to be capable of imaging at high resolutions, it becomes possible to ensure a predetermined resolution (such as full HD image quality, for example), while also displaying an image on the display apparatus 200 having a large display screen, such as 50 inches or more, for example. For this reason, visibility is improved for the surgeon watching the display screen. Also, by configuring the imaging member 120 to be capable of imaging at high resolutions, even if the captured image is enlarged by the electronic zoom function and displayed on the display screen of the display apparatus 200, it is still possible to ensure a predetermined resolution. Furthermore, in the case of using the electronic zoom function to ensure a predetermined resolution, since it is possible to reduce the performance of the optical zoom function in the imaging device 106, the optical system of the imaging device 106 can be simplified, and the imaging device 106 can be configured more compactly.

In the imaging device 106, for example, various operating devices for controlling the operation of the imaging device 106 are provided. For example, in FIG. 3, a zoom switch 124, a focus switch 126, and an operating mode change switch 128 are provided on the imaging device 106. Note that the positions and shapes in which to provide the zoom switch 124, the focus switch 126, and the operating mode change switch 128 obviously are not limited to the example illustrated in FIG. 3.

The zoom switch 124 and the focus switch 126 are an example of an operating device for adjusting the imaging parameters in the imaging device 106.

The zoom switch 124 includes, for example, a zoom-in switch 124*a* that increases the zoom magnification (enlargement ratio), and a zoom-out switch 124*b* that decreases the zoom magnification. By performing an operation on the zoom switch 124, the zoom magnification is adjusted, and the zoom is adjusted.

The focus switch 126 includes, for example, a long-range focus switch 126a that increases the focal length to the observation target (subject), and a close-range focus switch 126b that decreases the focal length to the observation target. By performing an operation on the focus switch 126, the focal length is adjusted, and the focus is adjusted.

The operating mode change switch 128 is an example of an operating device for changing the operating mode of the arm 104 in the imaging device 106. By performing an operation on the operating mode change switch 128, the operating mode of the arm 104 is changed. Examples of operating modes of the arm 104 include a locked mode and a free mode, as described above.

One example of an operation with respect to the operating mode change switch 128 is an operation of pressing the operating mode change switch 128. For example, the operating mode of the arm 104 becomes the free mode while the surgeon is pressing the operating mode change switch 128, and the operating mode of the arm 104 becomes the locked mode when the surgeon is not pressing the operating mode change switch 128.

In addition, the imaging device 106 is provided with, for example, an anti-slip member 130 and a projecting member 132 in order to further raise operability, convenience, and the like when an operator who performs operations on various operation devices performs an operation.

The anti-slip member 130 is a member provided to prevent slipping of an operating body such as a hand when, for example, the operator performs an operation on the barrel member 122 with the operating body. The anti-slip member 130 is formed with a material having a large coefficient of friction, for example, and has a slip-resistant structure due to unevenness or the like.

The projecting member 132 is member provided to prevent an operating body such as a hand blocking the field of view of the optical system 120a when the operator performs an operation on the barrel member 122 with the operating body, or to prevent a cover glass (not illustrated) from becoming dirty due to the cover glass being contacted by the operating body when an operation is performed with the operating body.

Note that the position and shape in which each of the anti-slip member 130 and the projecting member 132 is provided obviously are not limited to the example illustrated in FIG. 3. In addition, the imaging device 106 does not have to be provided with one or both of the anti-slip member 130 and the projecting member 132.

The image signal (image data) generated by imaging in the imaging device 106 is subjected to image processing in a processor that functions as the control section described later, for example. Examples of image processing according to the present embodiment include one or multiple processes from among various processes such as gamma correction, white balance adjustment, image enlargement or reduction related to the electronic zoom function, and pixel interpolation, for example.

Note that in the case in which the medical observation system according to the present embodiment includes a medical control apparatus (not illustrated) that controls various operations in the medical observation apparatus 100, the image processing according to the present embodiment may also be performed in the medical control apparatus (not illustrated).

For example, the medical observation apparatus 100 transmits a display control signal and the image signal subjected to image processing as described above to the display apparatus 200.

By transmitting the display control signal and the image signal to the display apparatus 200, on the display screen of the display apparatus 200, a medical captured image in which the observation target is imaged (for example, a captured image in which the operating site is imaged) is displayed enlarged or reduced at a desired magnification by one or both of the optical zoom function and the electronic zoom function.

The medical observation apparatus 100 illustrated in FIG. 1 includes the hardware configuration illustrated with reference to FIGS. 1 and 3, for example.

Note that the hardware configuration of the medical observation apparatus according to the present embodiment is not limited to the configuration illustrated with reference to FIGS. 1 and 3.

For example, the medical observation apparatus according to the present embodiment may also be a configuration not provided with the base 102, in which the arm 104 is directly attached to the ceiling, a wall, or the like of the operating room or the like. For example, in the case in which the arm 104 is attached to the ceiling, the medical observation apparatus according to the present embodiment becomes a configuration in which the arm 104 hangs down from the ceiling.

Also, although FIG. 1 illustrates an example in which the arm 104 is configured so that six degrees of freedom are realized with respect to the driving of the imaging device 106, the configuration of the arm 104 is not limited to a configuration whereby the degrees of freedom with respect to the driving of the imaging device 106 become six degrees of freedom. For example, it is sufficient to configure the arm 104 so that the imaging device 106 can move appropriately in accordance with the application, and factors such as the number and arrangement of joint sections and links, and the directions of the drive shafts of the joint sections can be set appropriately so that the arm 104 has the desired degrees of freedom.

Also, although FIGS. 1 and 3 illustrate an example in which various types of operating devices for controlling the operation of the imaging device 106 are provided on the imaging device 106, some or all of the operating devices illustrated in FIGS. 1 and 3 may also not be provided on the imaging device 106. To give one example, the various types of operating devices for controlling the operation of the imaging device 106 may also be provided in another part other than the imaging device 106 included in the medical observation apparatus according to the present embodiment. Also, to give another example, the various types of operating devices for controlling the operation of the imaging device 106 may also be external operating devices, such as a footswitch FS or a remote controller.

Additionally, the imaging device 106 may also have a configuration enabling switching among multiple observation modes. Observation modes according to the present embodiment may include, for example, an observation mode that executes imaging with natural light, an observation mode that executes imaging with special light, an observation mode that executes imaging by utilizing an image-enhancing observation technology such as narrow-band imaging (NBI), and the like. Special light according to the present embodiment refers to light in a specific wavelength band, such as light in the fluorescent wavelength band of fluorescent observation using 5-Aminolevulinic acid (5-ALA).

One example of the configuration of the imaging device 106 enabling switching among multiple observation modes is a "configuration provided with a filter that allows light of a specific wavelength band to pass through while not allowing light of other wavelength bands to pass through, and a movement mechanism that selectively disposes the filter on the optical path", for example. The specific wavelength band that the filter according to the present embodiment allows to pass through may be, for example, the wavelength band of near-infrared rays (for example, the wavelength band from approximately 0.7 [micrometers] to 2.5 [micrometers]), the fluorescent wavelength band for fluorescent observation using 5-ALA (for example, the wavelength band from approximately 0.6 [micrometers] to 0.65 [micrometers]), the fluorescent wavelength band of indocyanine green (ICG) (for example, the wavelength band from approximately 0.82 [micrometers] to 0.85 [micrometers]), or the like.

Note that the imaging device 106 may also be provided with multiple filters that allow different wavelength bands to pass through. Also, although the above illustrates an example in which imaging is executed with the light of a specific wavelength band by disposing a filter on the optical path, the configuration of the imaging device 106 for executing imaging with the light of a specific wavelength band obviously is not limited to the example illustrated above.

[1-2] Medical Observation System According to Second Example

The medical observation system 1000 according to the present embodiment is not limited to the configuration illustrated in the first example illustrated in FIG. 1. Next, as another example of the medical observation system 1000, one example of a configuration of the medical observation system 1000 including the medical observation apparatus 100 that functions as an endoscopic apparatus will be described.

Figure 4:
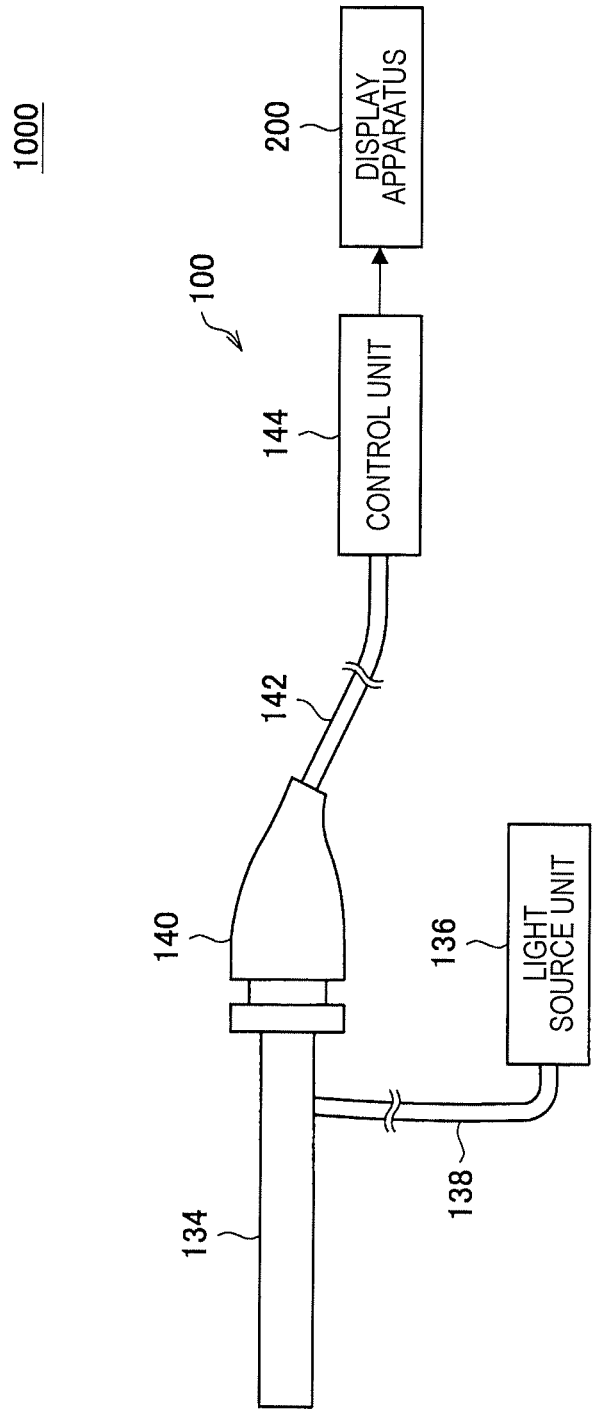
FIG. 4 is an explanatory diagram illustrating a second example of a configuration of a medical observation system according to the present embodiment.

FIG. 4 is an explanatory diagram illustrating a second example of the configuration of the medical observation system 1000 according to the present embodiment. The medical observation system 1000 illustrated in FIG. 4 includes the medical observation apparatus 100 and the display apparatus 200, for example. In the case in which the medical observation apparatus 100 illustrated in FIG. 4 is used during surgery, the surgeon observes the surgical site while referring to a medical captured image captured by the medical observation apparatus 100 and displayed on the display screen of the display apparatus 200, and performs various treatments, such as techniques depending on the surgical procedure, on the surgical site.

Note that the medical observation system according to the second example is not limited to the example illustrated in FIG. 4.

For example, the medical observation system according to the second example additionally may include a medical control apparatus (not illustrated) that controls various operations in the medical observation apparatus 100, similarly to the medical observation system according to the first example.

Also, the medical observation system according to the second example may be a configuration including a plurality of one or both of the medical observation apparatus 100 and the display apparatus 200, similarly to the medical observation system according to the first example.

Hereinafter, each apparatus included in the medical observation system 1000 according to the second example illustrated in FIG. 4 will be described.

[1-2-1] Display Apparatus 200

The display apparatus 200 is a display device in the medical observation system 1000 according to the second example, and corresponds to an external display device from the perspective of the medical observation apparatus 100. The display apparatus 200 included in the medical observation system 1000 according to the second example is similar to the display apparatus 200 included in the medical observation system 1000 according to the first example.

[1-2-2] Medical Observation Apparatus 100

The medical observation apparatus 100 illustrated in FIG. 4 is provided with an insertion member 134, a light source unit 136, a light guide 138, a camera head 140, a cable 142, and a control unit 144, for example. The medical observation apparatus 100 runs on electric power supplied from an internal power source such as a battery provided in the medical observation apparatus 100, on electric power supplied from a connected external power source, or the like, for example.

The insertion member 134 has an elongated shape, and is internally provided with an optical system that condenses incident light. The front end of the insertion member 134 is inserted inside a body cavity of a patient. The rear end of the insertion member 134 is detachably connected to the front end of the camera head 140. Also, the insertion member 134 is connected to the light source unit 136 through the light guide 138, and is supplied with light from the light source unit 136.

The insertion member 134 may be formed with an inflexible material or a flexible material. Depending on the material used to form the insertion member 134, the medical observation apparatus 100 may be called a rigid scope or a flexible scope.

The light source unit 136 is connected to the insertion member 134 through the light guide 138. The light source unit 136 supplies light to the insertion member 134 through the light guide 138.

For example, the light source unit 136 includes multiple light sources that emit light of different wavelengths. The multiple light sources included in the light source unit 136 may be, for example, a light source that emits red light, a light source that emits green light, and a light source that emits blue light. The light source that emits red light may be one or multiple red light-emitting diodes, for example. The light source that emits green light may be one or multiple green light-emitting diodes, for example. The light source that emits blue light may be one or multiple blue light-emitting diodes, for example. Note that the multiple light sources included in the light source unit 136 obviously are not limited to the example illustrated above. For example, the light source unit 136 includes the multiple light sources on a single chip or includes the multiple light sources on multiple chips.

The light source unit 136 is connected to the control unit 144 in a wired or wireless manner, and the light emission in the light source unit 136 is controlled by the control unit 144.

Light supplied to the insertion member 134 is emitted from the front end of the insertion member 134, and irradiates an observation target such as tissue inside the body cavity of the patient. Additionally, reflected light from the observation target is condensed by the optical system inside the insertion member 134.

The camera head 140 has a function of imaging the observation target. The camera head 140 is connected to the control unit 144 through a signal transmission member, namely the cable 142.

The camera head 140 includes an image sensor, images the observation target by photoelectrically converting the reflected light from the observation target condensed by the insertion member 134, and outputs an image signal obtained by the imaging (a signal expressing the medical captured image) to the control unit 144 through the cable 142. The image sensor included in the camera head 140 may be, for example, an image sensor using multiple imaging elements such as CMOS and CCD elements.

In the medical observation apparatus 100 that functions as an endoscopic apparatus, for example, the insertion member 134, the light source unit 136, and the camera head 140 fulfill the role of an "imaging device that is inserted inside a body of a patient and images the inside of the body".

Note that the medical observation apparatus 100 that functions as an endoscopic apparatus may also be a configuration provided with multiple imaging devices that function as what is called a stereo camera, for example. In a configuration of imaging devices that function as a stereo camera, similarly to the medical observation apparatus 100 included in the medical observation system according to the first example, the optical system may be a Galileo optical system or a Greenough optical system.

The control unit 144 controls the imaging device. More specifically, the control unit 144 controls each of the light source unit 136 and the camera head 140.

Also, the control unit 144 includes a communication device (not illustrated), and transmits an image signal output from the camera head 140 to the display apparatus 200 by any form of wireless communication or any form of wired communication. The control unit 144 may also transmit an image signal and a display control signal to the display apparatus 200.

The communication device (not illustrated) included in the control unit 144 may be, for example, an IEEE 802.15.1 port and a transmitting-receiving circuit (wireless communication), an IEEE 802.11 port and a transmitting-receiving circuit (wireless communication), a communication antenna and an RF circuit (wireless communication), an optical communication device (wireless communication or wired communication), a LAN terminal and a transmitting-receiving circuit (wired communication), or the like. The communication device (not illustrated) may also be a configuration capable of communicating with one or multiple external apparatus by multiple communication methods.

In addition, the control unit 144 may execute predetermined processing on the image signal output from the camera head 140, and transmit the image signal that has been subjected to the predetermined processing to the display apparatus 200. The predetermined processing on the image signal may be, for example, white balance adjustment, image enlargement or reduction according to an electronic zoom function, pixel interpolation, and the like.

Note that the control unit 144 may also store a medical captured image based on the image signal.

The control unit 144 may be a camera control unit (CCU), for example.

The medical observation apparatus 100 that functions as an endoscopic apparatus includes the hardware configuration illustrated with reference to FIG. 4, for example. In the medical observation apparatus 100 that functions as an endoscopic apparatus, for example, the insertion member 134, the light source unit 136, and the camera head 140 fulfill the role of the imaging device, and imaging in the imaging device is controlled by the control unit 144.

[1-3] Functional Configuration of Medical Observation Apparatus 100

Figure 5:
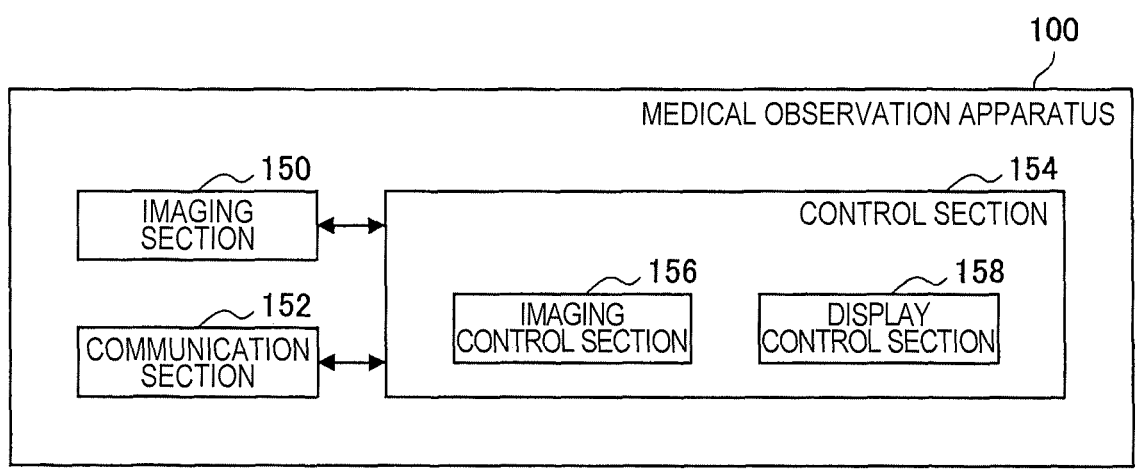
FIG. 5 is a function block diagram illustrating one example of a configuration of a medical observation apparatus according to the present embodiment.

Next, the medical observation apparatus 100 illustrated in FIGS. 1 and 4 will be described using function blocks. FIG. 5 is a function block diagram illustrating one example of the configuration of the medical observation apparatus 100 according to the present embodiment.

For example, the medical observation apparatus 100 is provided with an imaging section 150, a communication section 152, and a control section 154.

The imaging section 150 images the observation target. For example, the imaging section 150 includes the "imaging device 106" (in the case of the medical observation apparatus 100 illustrated in FIG. 1), or the "insertion member 134, the light source unit 136, and the camera head 140" (in the case of the medical observation apparatus 100 illustrated in FIG. 4). Imaging in the imaging section 150 is controlled by the control section 154, for example.

The communication section 152 is a communication device provided in the medical observation apparatus 100, and fulfills a role of communicating in a wireless or wired manner with an external apparatus such as the display apparatus 200. The communication section 152 includes the communication device (not illustrated) described above, for example. Communication in the communication section 152 is controlled by the control section 154, for example.

The control section 154 includes the processor (not illustrated) described above, for example, and fulfills a role of controlling the medical observation apparatus 100 overall. In addition, the control section 154 fulfills a role of leading the execution of the processes related to the display control method described later. Note that the processes related to the display control method in the control section 154 may also be executed in a distributed manner by multiple processing circuits (such as multiple processors, for example).

More specifically, the control section 154 includes an imaging control section 156 and a display control section 158, for example.

The imaging control section 156 controls the imaging device included in the imaging section 150. Examples of the control of the imaging device include control of one or multiple functions typically provided in an electronic imaging microscope section, such as control of an AF function, including at least a zoom function (one or both of an optical zoom function and an electronic zoom function).

The display control section 158 executes the processes related to the display control method according to the present embodiment, controlling the display of the medical captured image on the display screen and controlling the display of a pointer object on the display screen.

The control of the display of the medical captured image on the display screen in the display control section 158 may be, for example, control causing each of a medical captured image for the right eye and a medical captured image for the left eye to be displayed on the display screen (3D display control). Note that the display control section 158 is also capable of performing a 2D display control by causing either the medical captured image for the right eye or the medical captured image for the left eye to be displayed. The following gives an example of a case in which the display control section 158 causes each of the medical captured image for the right eye and the medical captured image for the left eye to be displayed on the display screen.

The pointer object according to the present embodiment is one example of a display object to be displayed on the display screen. By being displayed on the display screen, the pointer object fulfills a role of pointing to a region in the medical captured image being displayed on the display screen. It is possible to treat the region in the medical captured image pointed out by the pointer object as an annotation region.

The shape and size of the region pointed out by the pointer object may vary depending on the shape and size of the pointer object. The shape of the pointer object may be a preset fixed shape or a shape that is changeable on the basis of an operation by the user of the medical observation apparatus 100. Also, the size of the pointer object is changeable on the basis of an operation by the user of the medical observation apparatus 100, such as the region setting operation described later, for example.

The pointer object is displayed in a set display color. The display color of the pointer object may be a preset fixed color or a color that is changeable on the basis of an operation by the user of the medical observation apparatus 100 or the like. In addition, the display color of the pointer object may also be set automatically to be a color corresponding to the medical captured image displayed on the display screen by the processes related to the display control method according to the present embodiment described later.

By executing the processes related to the display control method according to the present embodiment, the display control section 158 causes the pointer object to be displayed in correspondence with the depth position of the medical captured image for the right eye and the medical captured image for the left eye, for example. One example of the processes related to the display control method according to the present embodiment and one example of the pointer object according to the present embodiment will be described later.

Additionally, for example, the display control section 158 controls the display on the display apparatus 200 by conveying the display control signal and the image signal to the communication device (not illustrated) included in the communication section 152, and causing the display control signal and the image signal to be transmitted to the display apparatus 200. Note that the control of communication in the communication section 152 may also be performed by a communication control section (not illustrated) included in the control section 154.

Additionally, the display control section 158 may also cause data corresponding to the image signal to be recorded to any recording medium, such as a recording medium (not illustrated) that functions as a storage section (not illustrated) or an external recording medium. The data corresponding to the image signal to be recorded to a recording medium may be data in which the pointer object is superimposed onto the medical captured image as described later or data expressing the medical captured image without the pointer object superimposed as described later. The data in which the pointer object is superimposed onto the medical captured image as described later may be, for example, data in which the pointer object is composited onto the medical captured image. Note that the data indicating the pointer object and the data indicating the medical captured image may be recorded in association with each other by any method. The above data indicating the pointer object is recorded as 3D information, for example, and when the pointer object is displayed together with the medical captured image, the pointer object is displayed superimposed onto the medical captured image. For example, by storing data in which the pointer object is superimposed onto the medical captured image as described later in a recording medium, it becomes possible to use the data for various purposes, such as postoperative examination purposes and educational purposes.

For example, by including the display control section 158, the control section 154 fulfills a role of leading the execution of the processes related to the display control method according to the present embodiment. Also, for example, by including the imaging control section 156 and the display control section 158, the control section 154 fulfills a role of controlling the medical observation apparatus 100 overall.

Note that the functional configuration of the control section 154 is not limited to the example illustrated in FIG. 5.

For example, it is possible for the control section 154 to have any configuration corresponding to how the functions included in the medical observation apparatus 100 are divided up, such as a configuration corresponding to how the processes related to the display control method according to the present embodiment are divided up.

To give one example, in the case in which the medical observation apparatus 100 has the configuration illustrated in FIG. 1, the control section 154 additionally may include an arm control section (not illustrated) that controls the driving of the arm 104. One example of control of the driving of the arm 104 includes, for example, "applying a control signal that controls driving to the actuators (not illustrated) corresponding to each of the joint sections 110*a*, 110*b*, 110*c*, 110*d*, 110*e*, and 110*f*", and the like.

The medical observation apparatus 100 performs processes related to the display control method according to the present embodiment described later with the functional configuration illustrated in FIG. 5, for example.

Note that the functional configuration of the medical observation apparatus according to the present embodiment is not limited to the configuration illustrated in FIG. 5.

For example, in the medical observation apparatus according to the present embodiment, one or both of the imaging control section 156 and the display control section 158 illustrated in FIG. 5 can be provided separately from the control section 154 (for example, realized by a different processing circuit).

Additionally, in the medical observation apparatus according to the present embodiment, the functional configuration capable of executing the processes related to the display control method according to the present embodiment is not limited to the configuration illustrated in FIG. 5, and it is possible for the medical observation apparatus according to the present embodiment to take a functional configuration corresponding to how the processes related to the display control method according to the present embodiment are divided up.

Also, in the case in which the medical observation apparatus according to the present embodiment has the configuration illustrated in FIG. 1, the medical observation apparatus according to the present embodiment includes an arm section (not illustrated) including the arm 104. The arm 104 included in the arm section (not illustrated) supports the imaging device 106 included in the imaging section 150.

Also, for example, in the case of communicating with an external apparatus via an external communication device having a function and configuration similar to the communication section 152, the medical observation apparatus according to the present embodiment may also not be provided with the communication section 152.

Also, in the case in which the medical observation system according to the present embodiment includes a medical control apparatus (not illustrated), and the medical observation apparatus according to the present embodiment is controlled by the medical control apparatus (not illustrated), the medical observation apparatus according to the present embodiment may also not be provided with the control section 154.

Herein, the medical control apparatus (not illustrated) is, for example, provided with a control section having a function and configuration similar to the control section 154, and thereby executes processes related to the display control method according to the present embodiment described later, and in addition, controls the operation in each structural element such as the imaging section 150 provided in the medical observation apparatus according to the present embodiment. The medical control apparatus (not illustrated) communicates with the medical observation apparatus according to the present embodiment via a provided communication device or a connected external communication device, and thereby controls the operation in each structural element provided in the medical observation apparatus according to the present embodiment.

Furthermore, in the case in which the medical observation system according to the present embodiment includes the medical control apparatus (not illustrated), and the medical observation apparatus according to the present embodiment is controlled by the medical control apparatus (not illustrated), it is also possible for the medical observation apparatus according to the present embodiment to take a configuration that does not include some of the functions of the control section 154.

[2] Display Control Method According to Present Embodiment

Next, the display control method according to the present embodiment will be described. The following gives an example of a case in which the processes related to the display control method according to the present embodiment are executed by the medical observation apparatus 100 (more specifically, the display control section 158 of the control section 154 included in the medical observation apparatus 100, for example). Note that, as described above, in the medical observation system according to the present embodiment, the processes related to the display control method according to the present embodiment may also be executed by the display apparatus 200, a medical control apparatus (not illustrated), or the like.

[2-1] Processes Related to Display Control Method According to Present Embodiment As described above, in the medical field, in the case in which an electronic imaging medical observation apparatus like the medical observation apparatus 100 is used, the medical captured image displayed on the display screen of a display apparatus 200 is viewed by multiple persons such as medical personnel members. Also, in the above case, when one person attempts to inform another person of a specific location to pay attention to in the medical captured image being displayed on the display screen, oral instructions are used. However, with verbal communication such as oral instructions, it may be difficult to convey the above location of attention appropriately in some cases.

Accordingly, the medical observation apparatus 100 causes the medical captured image to be displayed on the display screen while also causing a pointer object to be displayed on the display screen. By displaying the pointer object on the display screen where the medical captured image is being displayed, each person viewing the display screen is able to visually recognize the region pointed out by the pointer object. Therefore, a location to pay attention to in the medical captured image being displayed on the display screen may be conveyed more appropriately than in the case of conveying the location of attention by verbal communication, while in addition, it is possible to convey the location of attention to each person viewing the display screen at the same time. Therefore, by the medical observation apparatus 100 causing the pointer object to be displayed on the display screen, improved convenience for persons viewing a display screen on which a medical captured image is displayed may be achieved.

Also, in the case in which a location of attention in the medical captured image is pointed out by the pointer object as above, to further raise precision in conveying the location of attention, it is desirable to make the location pointed out by the pointer object (in other words, the site of the observation target pointed out by the pointer object) distinct.

Accordingly, in the case of causing a medical captured image for the right eye and a medical captured image for the left eye to be displayed, that is, in the case of causing each person viewing the display screen to recognize the medical captured image as a stereoscopic image, the medical observation apparatus 100 causes the pointer object to be displayed in correspondence with the depth position of the medical captured image for the right eye and the medical captured image for the left eye.

The depth position of the medical captured image for the right eye and the medical captured image for the left eye is specified by obtaining the "distance at each of the corresponding positions in the medical captured image for the right eye and the medical captured image for the left eye", for example. The depth position of the medical captured image for the right eye and the medical captured image for the left eye is also called the image depth. In the following, the depth position of the medical captured image for the right eye and the medical captured image for the left eye will also be designated the "image depth" in some cases.

The "distance at each of the corresponding positions in the medical captured image for the right eye and the medical captured image for the left eye" is obtained by executing the process in (a) and the process in (b) below, for example. The process in (a) and the process in (b) below may be executed by the medical observation apparatus 100 or by an apparatus external to the medical observation apparatus 100, such as a medical control apparatus (not illustrated). The following gives an example of a case in which the process in (a) and the process in (b) below are executed by the medical observation apparatus 100.

(a) Association Process

For example, the medical observation apparatus 100 associates the medical captured image for the right eye and the medical captured image for the left eye by extracting a characteristic portion from each of the medical captured image for the right eye and the medical captured image for the left eye and matching the extracted characteristic portions.

The characteristic portion in a medical captured image is extracted by using any technology capable of extracting a characteristic portion from an image, such as one or both of edges detected by any edge detection process and the result of any perimeter survey process, for example. Also, the medical observation apparatus 100 associates the medical captured image for the right eye and the medical captured image for the left eye by using any technology capable of comparing extracted characteristic portions to identify the same subject, such as pattern matching, for example.

(b) Distance Computing Process

The medical observation apparatus 100 computes a distance (image depth) corresponding to the depth position for each corresponding point associated by the process in (a) above (association process).

The medical observation apparatus 100 computes a distance z (image depth) by performing the arithmetic operations illustrated in Formula 1 below, for example. In Formula 1 below, "h" is a known value of the distance between the imaging device that captures the medical captured image for the right eye and the imaging device that captures the medical captured image for the left eye (in other words, the baseline length). In Formula 1 below, "f" is a known value of the focal length of the imaging device that captures the medical captured image for the right eye and the imaging device that captures the medical captured image for the left eye. In Formula 1 below, "x" represents the x-coordinate of a corresponding point in the medical captured image for the left eye, and "x'" represents the x-coordinate of a corresponding point in the medical captured image for the right eye.

$$z = h \cdot f / |x - x'| \quad \text{(Formula 1)}$$

For example, by executing the process in (a) above and the process in (b) above, it is possible to obtain the "distance at each of the corresponding positions in the medical captured image for the right eye and the medical captured image for the left eye". Note that processes capable of obtaining the "distance at each of the corresponding positions in the medical captured image for the right eye and the medical captured image for the left eye" obviously are not limited to the process in (a) above and the process in (b) above.

By "adjusting the depth position of the pointer object and causing the pointer object with the adjusted depth position to be displayed", the medical observation apparatus 100 achieves "causing the pointer object to be displayed in correspondence with the depth position of the medical captured image for the right eye and the medical captured image for the left eye".

Adjusting the depth position of the pointer object corresponds to, for example, "adjusting 'z' illustrated in Formula 1 above in relation to a pointer object for the right eye pointing to a region in the medical captured image for the right eye and a pointer object for the left eye pointing to a region in the medical captured image for the left eye".

The medical observation apparatus 100 adjusts the depth position of the pointer object such that the depth position of the pointer object approaches the depth position of the medical captured image for the right eye and the medical captured image for the left eye.

By displaying the pointer object with the adjusted depth position as above, it becomes possible to approach a sense of depth of the medical captured image for the right eye and the medical captured image for the left eye perceived by the persons viewing the display screen and a sense of depth of the pointer object perceived by the persons viewing the display screen. Also, if the sense of depth of the medical captured image for the right eye and the medical captured image for the left eye and the sense of depth of the pointer object perceived by the persons viewing the display screen become the same, it is possible to cause the persons viewing the display screen to recognize the location pointed out by the pointer object more distinctly.

Therefore, the medical observation apparatus 100 adjusts the depth position of the pointer object such that the sense of depth of the pointer object becomes the sense of depth of the medical captured image for the right eye and the medical captured image for the left eye, and causes the pointer object with the adjusted depth position to be displayed.

To give a specific example, the medical observation apparatus 100 adjusts the depth position of the pointer object to the depth position of the medical captured image for the right eye and the medical captured image for the left eye, for example. Note that the medical observation apparatus 100 may also adjust the depth position of the pointer object such that the "difference between the depth position of the pointer object and the depth position of the medical captured image for the right eye and the medical captured image for the left eye" becomes less than or equal to a set threshold value (or such that the difference becomes less than the threshold value), for example. The above threshold value may be a preset fixed value, or a variable value that is changeable on the basis of an operation by the user of the medical observation apparatus 100 or the like.

The medical observation apparatus 100 controls the display of the pointer object on the display screen on the basis of a predetermined operation.

Examples of types of predetermined operations according to the present embodiment include the operations illustrated below.

- Move operation: an operation for moving the pointer object
- Region setting operation: an operation for setting the region pointed out by the pointer object (for example, an operation enabling one or both of the shape of the pointer object and the size of the pointer object to be changed)
- Region deciding operation: an operation for deciding the region pointed out by the pointer object The predetermined operation according to the present embodiment may be any or all of an operation with respect to an operating device provided in the medical observation apparatus 100, an operation with respect to an external operating device such as a remote controller or the footswitch FS, a gesture-based operation (an operation performed by the motion of any recognition target for which a gesture is recognizable, such as line of sight or a hand), or a speech-based operation, for example.

The medical observation apparatus 100 determines that the predetermined operation has been performed in "the case in which an operation signal corresponding to an operation performed on any of various types of operating devices is detected", "the case in which a specific motion is detected from the motion of any recognition target, such as line of sight or a hand, obtained by executing a gesture recognition process of any type", or "the case in which specific speech is detected from a speech recognition result obtained by executing a speech recognition process of any type", for example. The motion data used to detect the specific motion above or character string data (or speech data) used to detect the specific speech above is stored in a recording medium (not illustrated) that functions as a storage section (not illustrated), for example. The above gesture recognition process of any type and the above speech recognition process of any type may be executed by the medical observation apparatus 100 or by an apparatus external to the medical observation apparatus 100, such as a medical control apparatus (not illustrated).

When it is determined that the predetermined operation has been performed, the medical observation apparatus 100 controls the display of the pointer object on the display screen in correspondence with the determined predetermined operation.

In the following, as a specific example of the processes related to the display control method according to the present embodiment, one example of a case in which the display of the pointer object is controlled on the basis of the predetermined operation will be described.

(1) First Example of Processes Related to Display Control Method According to Present Embodiment FIG. 6 is an explanatory diagram for explaining the first example of the processes related to the display control method according to the present embodiment, and illustrates one example of a case in which the move operation, the region setting operation, and the region deciding operation are performed consecutively as the predetermined operation. A of FIG. 6 illustrates one example of the display of the display screen in the case in which the move operation is performed, and B in FIG. 6 illustrates one example of the display of the display screen in the case in which the region setting operation is performed. C of FIG. 6 illustrates one example of the display of the display screen in the region deciding operation.

"O" illustrated in each of A, B, and C of FIG. 6 illustrates one example of a pointer object according to the present embodiment. Note that the shape and size of the pointer object according to the present embodiment obviously are not limited to the examples illustrated in each of A, B, and C of FIG. 6.

When it is determined that the move operation has been performed, as illustrated in A of FIG. 6 for example, the medical observation apparatus 100 causes the pointer object to move in correspondence with the determined move operation.

When it is determined that the region setting operation has been performed, as illustrated in B of FIG. 6 for example, the medical observation apparatus 100 increases the size of pointer object and widen the region pointed out by the pointer object in correspondence with the determined region setting operation. Note that it is also possible for the medical observation apparatus 100 to decrease the size of the pointer object and narrow the region pointed out by the pointer object in correspondence with the determined region setting operation.

When it is determined that the region deciding operation has been performed, as illustrated in C of FIG. 6 for example, the medical observation apparatus 100 causes the pointer object to be displayed in correspondence with the depth position of the medical captured image for the right eye and the medical captured image for the left eye. For example, like in the example illustrated in A and B of FIG. 6, in the case in which the pointer object is a circular object, the medical observation apparatus 100 deforms the circular object to match the depth position (image depth) of the medical captured image for the right eye and the medical captured image for the left eye.

Figure 7:
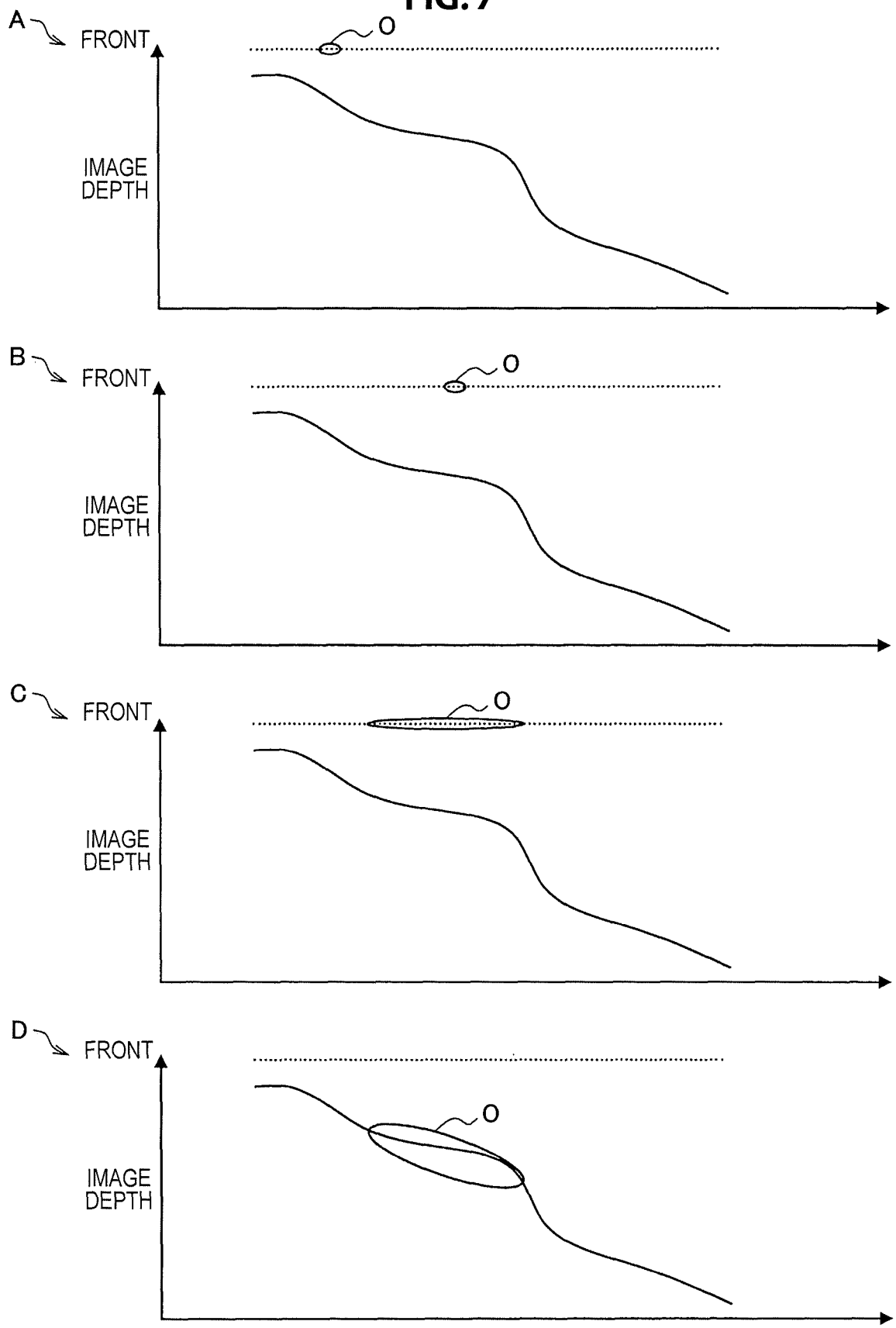
FIG. 7 is an explanatory diagram for explaining the first example of processes related to the display control method according to the present embodiment.

FIG. 7 is an explanatory diagram for explaining the first example of the processes related to the display control method according to the present embodiment, and is a diagram in which the example of the control of the pointer object as illustrated with reference to FIG. 6 is expressed with a different representation. For the sake of convenience, FIG. 7 illustrates an example of the control of the display of the pointer object corresponding to one among the medical captured image for the right eye and the medical captured image for the left eye. The horizontal axis in each of A, B, C, and D of FIG. 7 illustrates a certain horizontal line in the medical captured image. The vertical axis in each of A, B, C, and D of FIG. 7 illustrates the image depth. A and B of FIG. 7 correspond to the case in which the move operation illustrated in A of FIG. 6 is performed, while C of FIG. 7 corresponds to the case in which the region setting operation illustrated in B of FIG. 6 is performed. D of FIG. 7 corresponds to the case in which the region deciding operation illustrated in C of FIG. 6 is performed.

As illustrated in A, B, and C of FIG. 7, before the region deciding operation is performed, the medical observation apparatus 100 causes the pointer object to be displayed at a depth position in front of the depth position (image depth) of the medical captured image for the right eye and the medical captured image for the left eye.

Also, as illustrated in D of FIG. 7, in the case in which the region deciding operation is performed, the medical observation apparatus 100 causes the pointer object to be displayed in correspondence with the depth position (image depth) of the medical captured image for the right eye and the medical captured image for the left eye.

Note that in D of FIG. 7, a single pointer object O is indicated, but the medical observation apparatus 100 may also cause a pointer object for the right eye pointing to a region in the medical captured image for the right eye and a pointer object for the left eye pointing to a region in the medical captured image for the left eye to be displayed. In this case, the depth positions of each of the pointer object for the right eye and the pointer object for the left eye are adjusted to become the depth position of the medical captured image for the right eye and the medical captured image for the left eye, for example.

(2) Second Example of Processes Related to Display Control Method According to Present Embodiment Examples in which the display of the pointer object is controlled on the basis of a predetermined operation are not limited to the first example illustrated with reference to FIGS. 6 and 7.

In the case in which the move operation, the region setting operation, and the region deciding operation are performed consecutively as the predetermined operation, the medical observation apparatus 100 may also cause the pointer object to be displayed in correspondence with the depth position of the medical captured image for the right eye and the medical captured image for the left eye when each of the region setting operation and the region deciding operation is performed, for example.

In the case in which the processes related to the second example are executed, when the move operation is being performed, the pointer object moves in correspondence with the move operation, and as illustrated in A and B of FIG. 7, the pointer object is displayed at a depth position in front of the depth position (image depth) of the medical captured image for the right eye and the medical captured image for the left eye. Also, in the case in which the processes related to the second example are executed, when the region setting operation is performed, the size of the pointer object changes, while in addition, the pointer object is displayed in correspondence with the depth position of the medical captured image for the right eye and the medical captured image for the left eye, for example. Also, in the case in which the processes related to the second example are executed, when the region deciding operation is performed, the pointer object is displayed in correspondence with the depth position of the medical captured image for the right eye and the medical captured image for the left eye. Note that after the region setting operation or the region deciding operation is performed, in the case in which the move operation is performed again, the medical observation apparatus 100 may cause the pointer object to be displayed at a depth position in front of the depth position of the medical captured image for the right eye and the medical captured image for the left eye, or may cause the pointer object to be displayed in correspondence with the depth position of the medical captured image for the right eye and the medical captured image for the left eye.

(3) Third Example of Processes Related to Display Control Method According to Present Embodiment Examples in which the display of the pointer object is controlled on the basis of a predetermined operation are not limited to the first example above and the second example above.

In the case in which the move operation, the region setting operation, and the region deciding operation are performed consecutively as the predetermined operation, the medical observation apparatus 100 may also cause the pointer object to be displayed in correspondence with the depth position of the medical captured image for the right eye and the medical captured image for the left eye when each of the move operation, the region setting operation, and the region deciding operation is performed, for example.

In the case in which the processes related to the third example are executed, when the move operation is being performed, the pointer object moves in correspondence with the move operation, while in addition, the pointer object is displayed in correspondence with the depth position of the medical captured image for the right eye and the medical captured image for the left eye. Also, in the case in which the processes related to the third example are executed, when the region setting operation is performed, the size of the pointer object changes, while in addition, the pointer object is displayed in correspondence with the depth position of the medical captured image for the right eye and the medical captured image for the left eye, for example. Also, in the case in which the processes related to the third example are executed, when the region deciding operation is performed, the pointer object is displayed in correspondence with the depth position of the medical captured image for the right eye and the medical captured image for the left eye.

In other words, in the case in which the processes related to the third example are executed, the pointer object is displayed in correspondence with the depth position of the medical captured image for the right eye and the medical captured image for the left eye, regardless of the type of predetermined operation being performed.

Examples of controlling the display of the pointer object on the basis of the predetermined operation include the first example illustrated in (1) above to the third example illustrated in (3) above, for example. Note that examples of controlling the display of the pointer object on the basis of the predetermined operation obviously are not limited to the examples illustrated above.

By executing the processes related to the display control method according to the present embodiment, the medical observation apparatus 100 causes the pointer object to be displayed in correspondence with the depth position of the medical captured image for the right eye and the medical captured image for the left eye.

By displaying the pointer object in correspondence with the depth position of the medical captured image for the right eye and the medical captured image for the left eye, the persons viewing the display screen become able to grasp the location pointed out by the pointer object more distinctly.

Consequently, by causing the pointer object to be displayed in correspondence with the depth position of the medical captured image for the right eye and the medical captured image for the left eye, the medical observation apparatus 100 potentially is able to improve convenience for persons viewing the display screen on which the medical captured image is displayed compared to the case of simply causing the pointer object to be displayed on the display screen.

Note that the processes related to the display control method according to the present embodiment are not limited to the example illustrated above.

For example, the medical observation apparatus 100 may also control the display color of the pointer object to be a color corresponding to the medical captured image displayed on the display screen.

By the medical observation apparatus 100 controlling the display color of the pointer object to be a color corresponding to the medical captured image displayed on the display screen, the display color of the pointer object is changed according to the color of the medical captured image at the position on the display screen where the pointer object is displayed.

For example, the medical observation apparatus 100 sets the display color of the pointer object to a complementary color of the color of the medical captured image at the position on the display screen where the pointer object is displayed. By setting the display color of the pointer object to a complementary color of the above color of the medical captured image, an advantageous effect is exhibited whereby the pointer object stands out, making the pointer object easier to recognize. Note that the display color of the pointer object is not limited to a perfectly complementary color, and obviously may be any color capable of making the pointer object stand out when contrasted against the medical captured image.

Taking the circular pointer object O illustrated in FIG. 6 as an example, the display color of the pointer object may be the color of a frame prescribing the shape of the pointer object O. To give a specific example, in the case in which a bone of the patient acting as the observation target exists at the position on the display screen where the circular pointer object O illustrated in FIG. 6 is displayed, the medical observation apparatus 100 sets the display color of the pointer object O to black, that is, a complementary color of the bone color (white). Also, in the case in which blood of the patient acting as the observation target exists at the position on the display screen where the circular pointer object O illustrated in FIG. 6 is displayed, the medical observation apparatus 100 sets the display color of the pointer object O to cyan, that is, a complementary color of the blood color (red). Note that "examples of setting the display color of the pointer object to a complementary color of the color of the medical captured image at the position on the display screen where the pointer object is displayed" obviously are not limited to the examples illustrated above.

Note that the process of controlling the display color of the pointer object to be a color corresponding to the medical captured image displayed on the display screen is not limited to the example illustrated above.

For example, the medical observation apparatus 100 may also set the display color of the pointer object to a complementary color of a "specific color among the colors of the medical captured image included in the region pointed out by the pointer object". The above specific color may be, for example, the "color with the most color components among the colors of the medical captured image included in the region pointed out by the pointer object". For example, the medical observation apparatus 100 computes a histogram of the colors of the medical captured image included in the region pointed out by the pointer object, and specifies the above color with the most color components.

As above for example, in the case of setting the display color of the pointer object to a complementary color of the above specific color, the display color may be set uniformly. Also, since the display color of the pointer object is a complementary color of a specific color such as the above color with the most color components, an advantageous effect is exhibited whereby the pointer object stands out, making the pointer object easier to recognize.

[3] Example of Advantageous Effects Exhibited by Use of Display Control Method According to Present Embodiment By using the display control method according to the present embodiment, the advantageous effects illustrated below are exhibited, for example. Note that the advantageous effects exhibited by using the display control method according to the present embodiment obviously are not limited to the examples illustrated below.

- Because a location of attention that is desirable to pay attention to and recognize may be emphasized by the pointer object, it is possible to convey the location of attention on the display screen appropriately to multiple persons at the same time. Note that even when the pointer object is displayed, oral communication may still be performed.
- In the case in which the pointer object is displayed in addition to performing oral communication, since visual communication by the pointer object is added to the oral-only communication, more accurate communication becomes possible.
- Because a location of attention that is desirable to pay attention to and recognize may be emphasized by the pointer object, it is possible to convey the location of attention appropriately even to persons with limited medical knowledge.
- It is possible to control the display of the pointer object by performing a predetermined operation, and the predetermined operation may include an operation that do not make use of the hands, such as an operation by the footswitch FS or a gesture operation by line of sight or the like, for example. Therefore, for example, even in the case in which the surgeon is performing a medical procedure, the surgeon is still able to issue an instruction by the pointer object without using one's hands.
- The predetermined operation according to the control of the display of the pointer object may include an operation on an operating device that is operable by various persons not limited to the surgeon, such as an operation on a remote controller, for example. Therefore, the display of the pointer object may also be controlled by an operation by a person other than the persons present at the surgery venue, such as an attending physician looking at a display screen of a display apparatus in a different room from the surgery venue, for example.
- By causing data in which the pointer object is superimposed onto the medical captured image to be recorded to a recording medium, the data may be used for various purposes, such as postoperative examination purposes and educational purposes. As described above, the data in which the pointer object is superimposed onto the medical captured image may be, for example, data in which the pointer object is composited onto the medical captured image. Also, as described above, the data indicating the pointer object and the data indicating the medical captured image may be recorded in association with each other by any method.

Program According to Present Embodiment

By having a program (for example, a program capable of executing the processes related to the display control method according to the present embodiment) for causing a computer system to function as the medical observation apparatus according to the present embodiment (or the medical display control apparatus according to the present embodiment) be executed by a processor or the like in the computer system, it is possible to potentially improve convenience for persons viewing a display screen on which a medical captured image is displayed. At this point, the computer system according to the present embodiment may be a single computer or multiple computers. A series of processes related to the display control method according to the present embodiment is executed by the computer system according to the present embodiment.

Additionally, by having the program for causing a computer system to function as the medical observation apparatus according to the present embodiment (or the medical display control apparatus according to the present embodiment) be executed by a processor or the like in the computer system, the advantageous effects exhibited by the display realized by the processes related to the display control method according to the present embodiment described above can be exhibited.

It should be understood by those skilled in the art that various modifications, combinations, sub-combinations and alterations may occur depending on design requirements and other factors insofar as they are within the scope of the appended claims or the equivalents thereof.

For example, although the above illustrates the provision of a program (computer program) for causing a computer system to function as the medical observation apparatus according to the present embodiment (or the medical display control apparatus according to the present embodiment), in the present embodiment, the above program may also be provided in conjunction with a recording medium on which the above program is stored.

The configuration described above illustrates one example of the present embodiment, and rightfully belongs to the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification. Additionally, the present technology may also be configured as below.

(1) A medical display control apparatus including:

a display control section configured to control a display of a medical captured image for a right eye and a medical captured image for a left eye captured by an imaging device that images an observation target on a display screen and a display of a pointer object on the display screen, in which the display control section causes the pointer object to be displayed in correspondence with a depth position of the medical captured image for the right eye and the medical captured image for the left eye.

(2) The medical display control apparatus according to (1), in which the display control section adjusts a depth position of the pointer object, and causes the pointer object to be displayed in correspondence with the depth position of the medical captured image for the right eye and the medical captured image for the left eye.

(3) The medical display control apparatus according to (2), in which the display control section adjusts the depth position of the pointer object such that a sense of depth of the pointer object becomes a sense of depth of the medical captured image for the right eye and the medical captured image for the left eye.

(4) The medical display control apparatus according to (2) or (3), in which the display control section adjusts the depth position of the pointer object such that the depth position of the pointer object approaches the depth position of the medical captured image for the right eye and the medical captured image for the left eye.

(5) The medical display control apparatus according to (4), in which the display control section adjusts the depth position of the pointer object to the depth position of the medical captured image for the right eye and the medical captured image for the left eye.

(6) The medical display control apparatus according to any one of (1) to (5), in which the display control section controls the display of the pointer object on the display screen on the basis of a predetermined operation.

(7) The medical display control apparatus according to (6), in which before a region deciding operation that decides a region pointed out by the pointer object is performed, the display control section causes the pointer object to be displayed at a depth position in front of the depth position of the medical captured image for the right eye and the medical captured image for the left eye, and in a case in which the region deciding operation is performed, the display control section causes the pointer object to be displayed in correspondence with the depth position of the medical captured image for the right eye and the medical captured image for the left eye.

(8) The medical display control apparatus according to (6) or (7), in which on the basis of a move operation that moves the pointer object, the display control section causes the pointer object to be displayed at a position on the display screen corresponding to the move operation, and on the basis of a region setting operation that sets a region pointed out by the pointer object, the display control section changes a size of the pointer object to a size corresponding to the region setting operation.

(9) The medical display control apparatus according to any one of (1) to (8), in which the display control section sets a display color of the pointer object to a color corresponding to a medical captured image displayed on the display screen, and the display color of the pointer object is changed according to a color of the medical captured image at a position on the display screen where the pointer object is displayed.

(10) The medical display control apparatus according to (9), in which the display control section sets the display color of the pointer object to a complementary color of the color of the medical captured image at the position on the display screen where the pointer object is displayed.

(11) The medical display control apparatus according to (9), in which the display control section sets the display color of the pointer object to a complementary color of a specific color among colors of the medical captured image included in a region pointed out by the pointer object.

(12) The medical display control apparatus according to (11), in which the specific color is a color with the most color components among the colors of the medical captured image included in the region pointed out by the pointer object.

(13) The medical display control apparatus according to any one of (1) to (12), further including:

an arm including multiple links joined to each other by one or multiple joint sections; and the imaging device supported by the arm.

(14) The medical display control apparatus according to any one of (1) to (12), further including:

the imaging device that is inserted into an inside of a body of a patient and images the inside of the body as the observation target.

(15) A display control method executed by a medical display control apparatus, the display control method including:

controlling a display of a medical captured image for a right eye and a medical captured image for a left eye captured by an imaging device that images an observation target on a display screen and a display of a pointer object on the display screen, in which the controlling causes the pointer object to be displayed in correspondence with a depth position of the medical captured image for the right eye and the medical captured image for the left eye.

What is claimed is:

1. A medical display control apparatus comprising:
    processing circuitry configured to
        control a display of a medical captured image for a right eye and a medical captured image for a left eye captured by an imaging device that images an observation target on a display screen at a depth position of the medical captured image for the right eye and the medical captured image for the left eye;
        before receiving a region deciding operation that decides a region pointed out by a pointer object, control a display of the pointer object on the display screen at a depth position in front of the depth position of the medical captured image for the right eye and the medical captured image for the left eye;
        move the pointer object in accordance with a move operation that moves the pointer object, while keeping the depth position of the pointer object to be in front of the depth position of the medical captured image for the right eye and the medical captured image for the left eye;
        set at least one of a shape and a size of the pointer object in accordance with a region setting operation that sets the at least one of the shape and the size of the pointer object, while keeping the depth position of the pointer object to be in front of the depth position of the medical captured image for the right eye and the medical captured image for the left eye; and
        in response to receiving the region deciding operation, cause the pointer object to be displayed in correspondence with the depth position of the medical captured image for the right eye and the medical captured image for the left eye at a location designated by the move operation and with the at least one of the shape and the size of the pointer object designated by the region setting operation, and cause the depth position of the pointer object to correspond with the depth position of the medical captured image for the right eye and the medical captured image for the left eye.

2. The medical display control apparatus according to claim 1, wherein
the processing circuitry adjusts a depth position of the pointer object, and causes the pointer object to be displayed in correspondence with the depth position of the medical captured image for the right eye and the medical captured image for the left eye.

3. The medical display control apparatus according to claim 2, wherein
the processing circuitry adjusts the depth position of the pointer object such that a sense of depth of the pointer object becomes a sense of depth of the medical captured image for the right eye and the medical captured image for the left eye.

4. The medical display control apparatus according to claim 2, wherein
the processing circuitry adjusts the depth position of the pointer object such that the depth position of the pointer object approaches the depth position of the medical captured image for the right eye and the medical captured image for the left eye.

5. The medical display control apparatus according to claim 4, wherein
the processing circuitry adjusts the depth position of the pointer object to the depth position of the medical captured image for the right eye and the medical captured image for the left eye.

6. The medical display control apparatus according to claim 1, where
the processing circuitry controls the display of the pointer object on the display screen on a basis of a predetermined operation.

7. The medical display control apparatus according to claim 1, wherein
the processing circuitry sets a display color of the pointer object to a color corresponding to a medical captured image displayed on the display screen, and
the display color of the pointer object is changed according to a color of the medical captured image at a position on the display screen where the pointer object is displayed.

8. The medical display control apparatus according to claim 7, wherein
the processing circuitry sets the display color of the pointer object to a complementary color of the color of the medical captured image at the position on the display screen where the pointer object is displayed.

9. The medical display control apparatus according to claim 7, wherein
the processing circuitry sets the display color of the pointer object to a complementary color of a specific color among colors of the medical captured image included in a region pointed out by the pointer object.

10. The medical display control apparatus according to claim 9, wherein
the specific color is a color with the most color components among the colors of the medical captured image included in the region pointed out by the pointer object.

11. The medical display control apparatus according to claim 1, further comprising:
an arm including multiple links joined to each other by one or multiple joint sections; and
the imaging device supported by the arm.

12. The medical display control apparatus according to claim 1, further comprising:
the imaging device that is inserted into an inside of a body of a patient and images the inside of the body as the observation target.

13. The medical display control apparatus according to claim 1, wherein
the medical captured image for the right eye has different image depths according to locations inside the medical captured image for the right eye, and
the medical captured image for the left eye has different image depths according to locations inside the medical captured image for the left eye.

14. The medical display control apparatus according to claim 13, wherein
the processing circuitry is configured to cause the pointer object to be displayed at each of the different image depths inside the region pointed out by the pointer object for both the medical captured image for the right eye and the medical captured image for the left eye, such that image depth of the pointer object changes according to a location inside the region pointed out by the pointer object.

15. The medical display control apparatus according to claim 14, wherein
before receiving the region deciding operation that decides the region pointed out by the pointer object, the image depth of the pointer object is entirely at the depth position in front of the depth position of the medical captured age for the right eye and the medical captured image for the left eye, such that the image depth of the pointer object does not change according to the location inside the region pointed out by the pointer object.

16. A display control method executed by a medical display control apparatus, the display control method comprising:
controlling a display of a medical captured image for a right eye and a medical captured image for a left eye captured by an imaging device that images an observation target on a display screen at a depth position of the medical captured image for the right eye and the medical captured image for the left eye;
before receiving a region deciding operation that decides a region pointed out by a pointer object, control a display of the pointer object on the display screen at a depth position in front of the depth position of the medical captured image for the right eye and the medical captured image for the left eye;
moving the pointer object in accordance with a move operation that moves the pointer object, while keeping the depth position of the pointer object to be in front of the depth position of the medical captured image for the right eye and the medical captured image for the left eye;
setting at least one of a shape and a size of the pointer object in accordance with a region setting operation that sets the at least one of the shape and the size of the pointer object, while keeping the depth position of the pointer object to be in front of the depth position of the medical captured image for the right eye and the medical captured image for the left eye; and in response to receiving the region deciding operation, causing, using processing circuitry, the pointer object to be displayed in correspondence with the depth position of the medical captured image for the right eye and the medical captured image for the left eye at a location designated by the move operation and with the at least one of the shape and the size of the pointer object designated by the region setting operation, and causing the depth position of the pointer object to correspond with the depth position of the medical captured image for the right eye and the medical captured image for the left eye.

* * * * *